US011123095B2

(12) United States Patent
Conlon et al.

(10) Patent No.: US 11,123,095 B2
(45) Date of Patent: Sep. 21, 2021

(54) BLADE GROUNDING MECHANISMS AND ALTERNATIVE PIN DESIGNS

(71) Applicant: Ethicon LLC, Guaynabo, PR (US)

(72) Inventors: Sean P. Conlon, Loveland, OH (US); Ellen Burkart, Cincinnati, OH (US); Guion Y. Lucas, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 64 days.

(21) Appl. No.: 16/398,616

(22) Filed: Apr. 30, 2019

(65) Prior Publication Data

US 2020/0345389 A1 Nov. 5, 2020

(51) Int. Cl.

| A61B 17/32 | (2006.01) |
|---|---|
| A61B 18/14 | (2006.01) |
| A61B 17/00 | (2006.01) |
| A61B 18/00 | (2006.01) |

(52) U.S. Cl.
CPC .. *A61B 17/320092* (2013.01); *A61B 18/1445* (2013.01); *A61B 2017/0023* (2013.01); *A61B 2017/00367* (2013.01); *A61B 2017/320074* (2017.08); *A61B 2017/320088* (2013.01); *A61B 2017/320094* (2017.08); *A61B 2017/320095* (2017.08); *A61B 2018/00595* (2013.01); *A61B 2018/00994* (2013.01)

(58) Field of Classification Search
CPC ....... A61B 2017/320095; A61B 2017/320074; A61B 17/320068; A61B 2017/320094; A61B 2017/320088; A61B 2018/00607; A61B 2017/320093; A61B 2017/320097; A61B 2017/320098; A61B 17/3213; A61B 17/28; A61B 17/282; A61B 17/320092; A61B 2017/0046; A61B 2017/00464; A61B 2017/00477

See application file for complete search history.

(56) References Cited

U.S. PATENT DOCUMENTS

| 5,322,055 A | 6/1994 | Davison et al. |
|---|---|---|
| 5,324,299 A | 6/1994 | Davison et al. |
| 5,776,155 A | 7/1998 | Beaupre et al. |

(Continued)

FOREIGN PATENT DOCUMENTS

EP      1946708 B1      6/2011

OTHER PUBLICATIONS

U.S. Appl. No. 61/410,603, entitled "Energy-Based Surgical Instruments," filed Nov. 5, 2010.

(Continued)

*Primary Examiner* — Tan-Uyen T Ho
*Assistant Examiner* — Bridget E. Rabaglia
(74) *Attorney, Agent, or Firm* — Frost Brown Todd LLC

(57) ABSTRACT

A surgical instrument includes a body, a shaft assembly, and an end effector. The end effector includes an ultrasonic blade and a clamp arm movably coupled with the shaft assembly. The shaft assembly extends between the body and the end effector and includes an acoustic waveguide, a rotational driver, and a driver wrench. The rotational driver is configured to be received within the rotational drive channel and rotate the shaft assembly relative to the body. The acoustic waveguide includes a notch and the driver wrench includes a key, wherein the first notch of the acoustic waveguide is configured to receive the key.

20 Claims, 17 Drawing Sheets

(56) References Cited

U.S. PATENT DOCUMENTS

| | | | |
|---|---|---|---|
| 5,873,873 A | 2/1999 | Smith et al. | |
| 5,938,633 A | 8/1999 | Beaupre | |
| 5,954,736 A | 9/1999 | Bishop et al. | |
| 5,980,510 A | 10/1999 | Tsonton et al. | |
| 6,283,981 B1 | 9/2001 | Beaupre | |
| 6,309,400 B2 | 10/2001 | Beaupre | |
| 6,325,811 B1 * | 12/2001 | Messerly | A61B 17/320092 606/169 |
| 6,423,082 B1 | 7/2002 | Houser et al. | |
| 6,500,176 B1 | 12/2002 | Truckai et al. | |
| 6,773,444 B2 | 8/2004 | Messerly | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,189,233 B2 | 3/2007 | Truckai et al. | |
| 7,186,253 B2 | 5/2007 | Truckai et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,544,200 B2 | 6/2009 | Houser | |
| 8,057,498 B2 | 11/2011 | Robertson | |
| 8,435,258 B2 * | 5/2013 | Young | G10K 11/24 606/169 |
| 8,461,744 B2 | 6/2013 | Wiener et al. | |
| 8,591,459 B2 | 11/2013 | Clymer et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,911,460 B2 | 12/2014 | Neurohr et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,381,058 B2 | 5/2016 | Houser et al. | |
| 9,393,037 B2 | 7/2016 | Olson et al. | |
| 9,743,946 B2 | 8/2017 | Faller et al. | |
| 9,750,521 B2 | 9/2017 | Lamping et al. | |
| 9,795,379 B2 | 10/2017 | Leimbach et al. | |
| 9,949,785 B2 | 4/2018 | Price et al. | |
| 10,034,685 B2 | 7/2018 | Boudreaux et al. | |
| 10,172,636 B2 | 1/2019 | Stulen et al. | |
| 10,206,705 B2 | 2/2019 | Estera et al. | |
| 10,327,797 B2 | 6/2019 | Conlon et al. | |
| 10,349,967 B2 | 7/2019 | Hibner et al. | |
| 10,376,304 B2 | 8/2019 | Houser et al. | |
| 10,492,820 B2 | 12/2019 | Hibner et al. | |
| 10,603,129 B2 | 3/2020 | Roberson et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0105750 A1 | 4/2009 | Price et al. | |
| 2011/0015660 A1 | 1/2011 | Wiener et al. | |
| 2012/0116265 A1 | 5/2012 | Houser et al. | |
| 2015/0080924 A1 | 3/2015 | Stulen et al. | |
| 2015/0141981 A1 | 5/2015 | Price et al. | |
| 2016/0143659 A1 | 5/2016 | Glutz et al. | |
| 2017/0172615 A1 * | 6/2017 | Hibner | A61N 7/02 |
| 2019/0000499 A1 | 1/2019 | Stokes et al. | |
| 2019/0008546 A1 * | 1/2019 | Ruiz Ortiz | A61B 17/320092 |
| 2019/0029707 A1 * | 1/2019 | Asher | A61B 17/320092 |

OTHER PUBLICATIONS

International Search Report and Written Opinion dated Aug. 13, 2020 for Application No. PCT/IB2020/053467, 16 pgs.

* cited by examiner

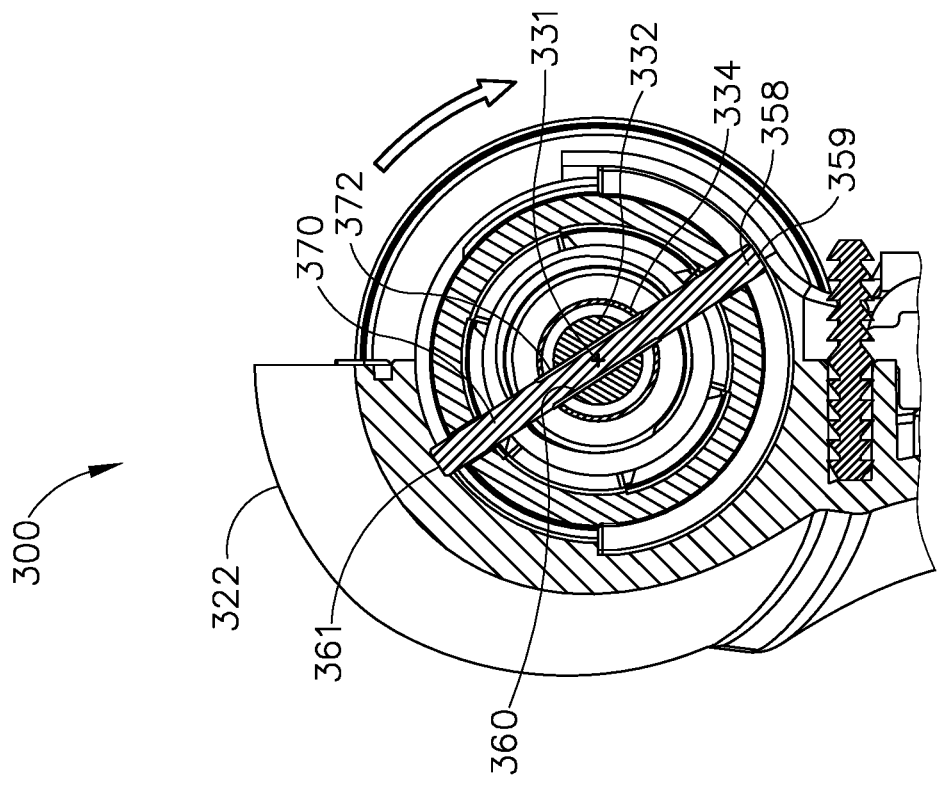
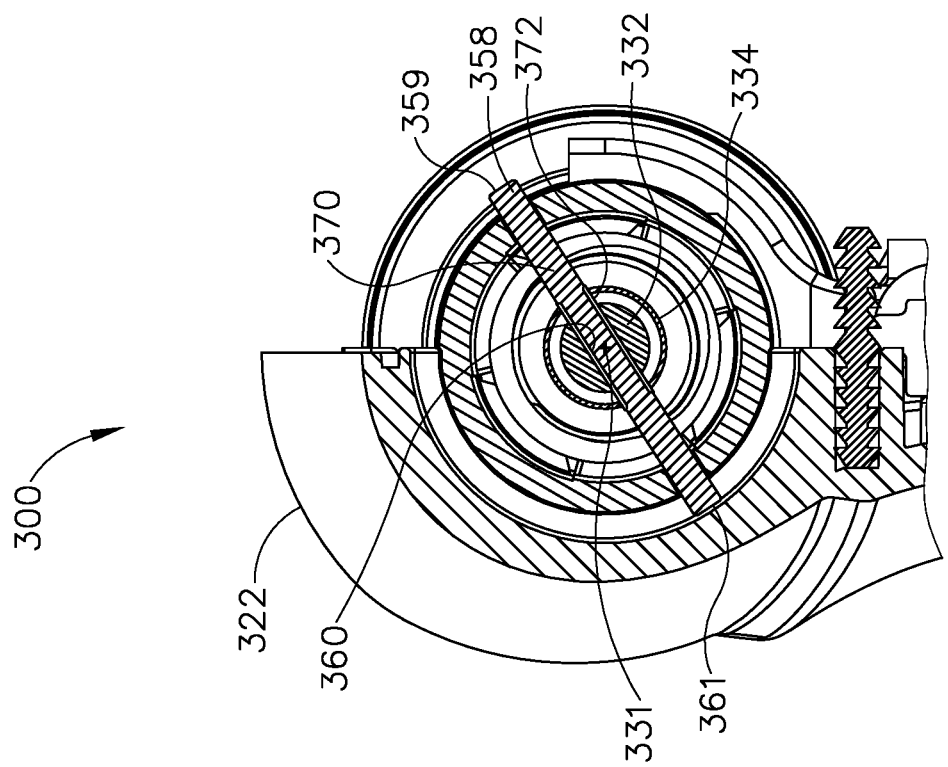

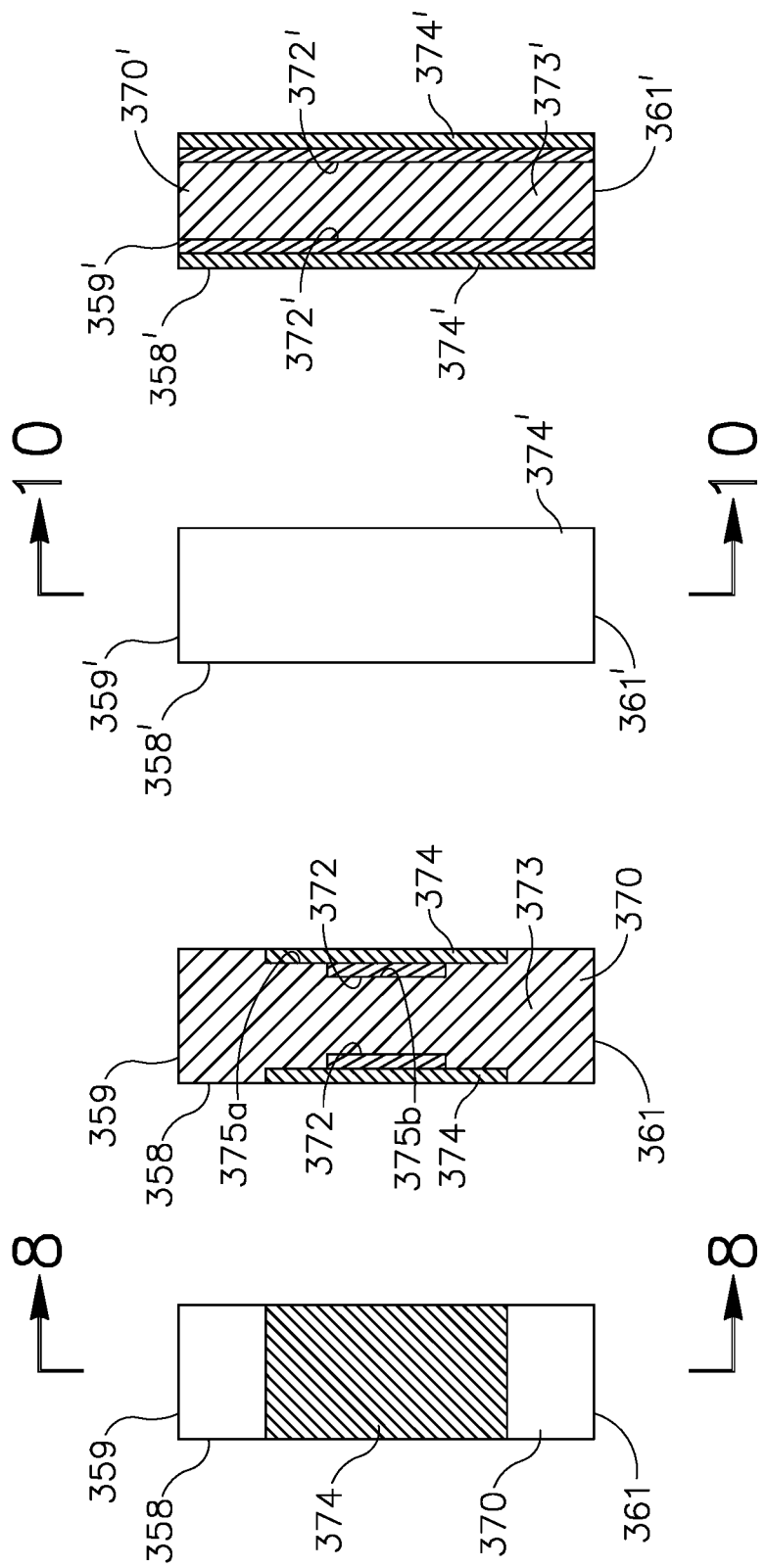

BLADE GROUNDING MECHANISMS AND ALTERNATIVE PIN DESIGNS

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; and U.S. Pat. No. 9,095,367, issued Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6A depicts an enlarged, cross-sectional view of a shaft assembly rotation system of the ultrasonic surgical instrument of FIG. 4 taken along section line 6A-6A of FIG. 4, showing a first example of a guide pin rotated to a first rotational position;

FIG. 6B depicts the enlarged, cross-sectional view of the shaft assembly rotation system of similar to FIG. 6A, but showing the guide pin rotated from the first rotational position to a second rotational position;

FIG. 7 depicts a front elevational view of the guide pin of FIG. 6A;

FIG. 8 depicts a cross-sectional view of the guide pin of FIG. 7 taken along section line 8-8 of FIG. 7;

FIG. 9 depicts a front elevational view of a second example of a guide pin;

FIG. 10 depicts a cross-sectional view of the guide pin of FIG. 9 taken along section line 10-10 of FIG. 9;

Figure 1:
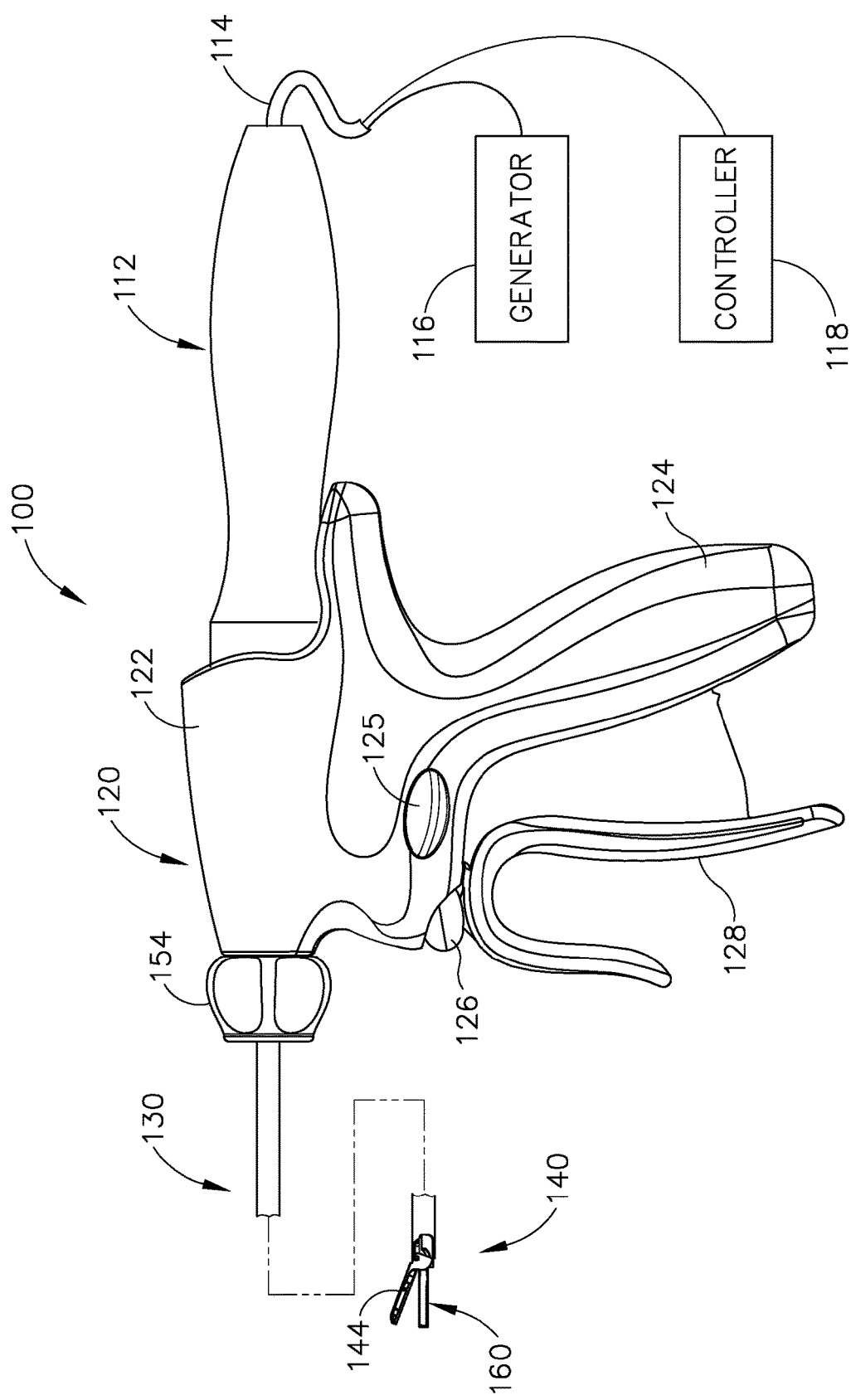
FIG. 1 depicts a side elevational view of a first exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument with Integrated Rf Energy

FIG. 1 illustrates an exemplary ultrasonic surgical instrument (100). At least part of instrument (100) may be constructed and operable in accordance with at least some of the teachings of any of the patent references that are cited herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades.

Instrument (100) of the present example comprises a body, such as a handle assembly (120), a shaft assembly (130), and an end effector (140). Handle assembly (120) includes a housing (122), a pistol grip (124), and a pair of buttons (125, 126). Handle assembly (120) also includes a clamp actuator (128), which may resemble a trigger, that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with clamp actuator (128) such that clamp arm (144) is pivotable toward ultrasonic blade (160) in response to pivoting of clamp actuator (128) toward pistol grip (124); and such that clamp arm (144) is pivotable away from ultrasonic blade (160) in response to pivoting of clamp actuator (128) away from pistol grip (124). Various suitable ways in which clamp arm (144) may be coupled with clamp actuator (128) are disclosed in various patent references cited herein; and further suitable ways in which clamp arm (144) may be coupled with clamp actuator (128) will be apparent to those of ordinary skill in the art in view of the teachings herein. In some versions, one or more resilient members are used to bias clamp arm (144) and/or clamp actuator (128) to the open position shown in FIG. 1. Further, in some versions, a rotation knob (154) is used to rotate shaft assembly (130) and end effector (140) about a longitudinal axis defined by the centerline of shaft assembly (130).

An ultrasonic transducer assembly (112) extends proximally from housing (122) in the present example. In some other versions, transducer assembly (112) is fully integrated within housing (122). Transducer assembly (112) is coupled with a generator (116) via a cable (114). Transducer assembly (112) receives electrical power from generator (116) and converts that electrical power into ultrasonic vibrations through piezoelectric principles as is known in the art. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, controller (118) and generator (116) may be integrated together in a single unit. By way of example only, generator (116) may comprise a GEN04 or GEN11 sold by Ethicon Endo-Surgery, Inc. of Cincinnati, Ohio. In addition, or in the alternative, generator (116) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad (not shown) that is secured to the underside of clamp arm (144), facing blade (160). By way of example only, the clamp pad (not shown) may be formed of a polytetrafluoroethylene (PTFE) material and/or any other suitable material(s). By way of further example only, the clamp pad (not shown) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of clamp actuator (128) toward pistol grip (124). Blade (160) of the present example is operable to vibrate at ultrasonic frequencies to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the acoustic waveguide and blade (160)

may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

End effector (140) of the present example is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (100) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition, or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pat. No. 9,949,785, entitled "Ultrasonic Surgical Instrument with Electrosurgical Feature," issued Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

Buttons (125, 126) may provide the operator with varied control of the energy that is applied to tissue through end effector (140). For instance, in some versions, button (125) may be activated to apply RF electrosurgical energy to tissue; while button (126) may be activated to apply ultrasonic energy to tissue. As another merely illustrative example, button (125) may be activated to apply ultrasonic energy to tissue at a low power level (e.g., without also applying RF electrosurgical energy to tissue, applying RF electrosurgical energy to tissue simultaneously, or applying RF electrosurgical energy to tissue in a sequence with the ultrasonic energy); while button (126) may be activated to apply ultrasonic energy to tissue at a high power level (e.g., without also applying RF electrosurgical energy to tissue, applying RF electrosurgical energy to tissue simultaneously, or applying RF electrosurgical energy to tissue in a sequence with the ultrasonic energy). In addition, or in the alternative, buttons (125, 126) may provide functionality in accordance with at least some of the teachings of U.S. Pat. No. 9,949, 785, entitled "Ultrasonic Surgical Instrument with Electrosurgical Feature," issued Apr. 24, 2018, the disclosure of which is incorporated by reference herein. Other suitable ways in which buttons (125, 126) may provide operation of instrument (100) will be apparent to those of ordinary skill in the art in view of the teachings herein.

II. Exemplary Ultrasonic Surgical Instrument with Combination of Reusable and Disposable Components In some instances, it may be desirable to provide a version of instrument (100) that is formed by a combination of components that are disposable (e.g., configured for use in only one surgical procedure) and components that are reusable (e.g., configured for use in more than one surgical procedure, subject to reprocessing and sterilization, etc., between surgical procedures). By way of example only, the disposable and reusable components of a surgical instrument may be assembled together to form the surgical instrument before a surgical procedure, the assembled surgical instrument may then be used to perform the surgical procedure, and then the disposable and reusable components of the surgical instrument may be disassembled after the surgical procedure is complete. Providing a disposable/reusable dichotomy among surgical instrument components may provide a reduction in cost and overall waste as compared to conventional instrumentations that are provided as an entirely disposable unit.

Figure 2:
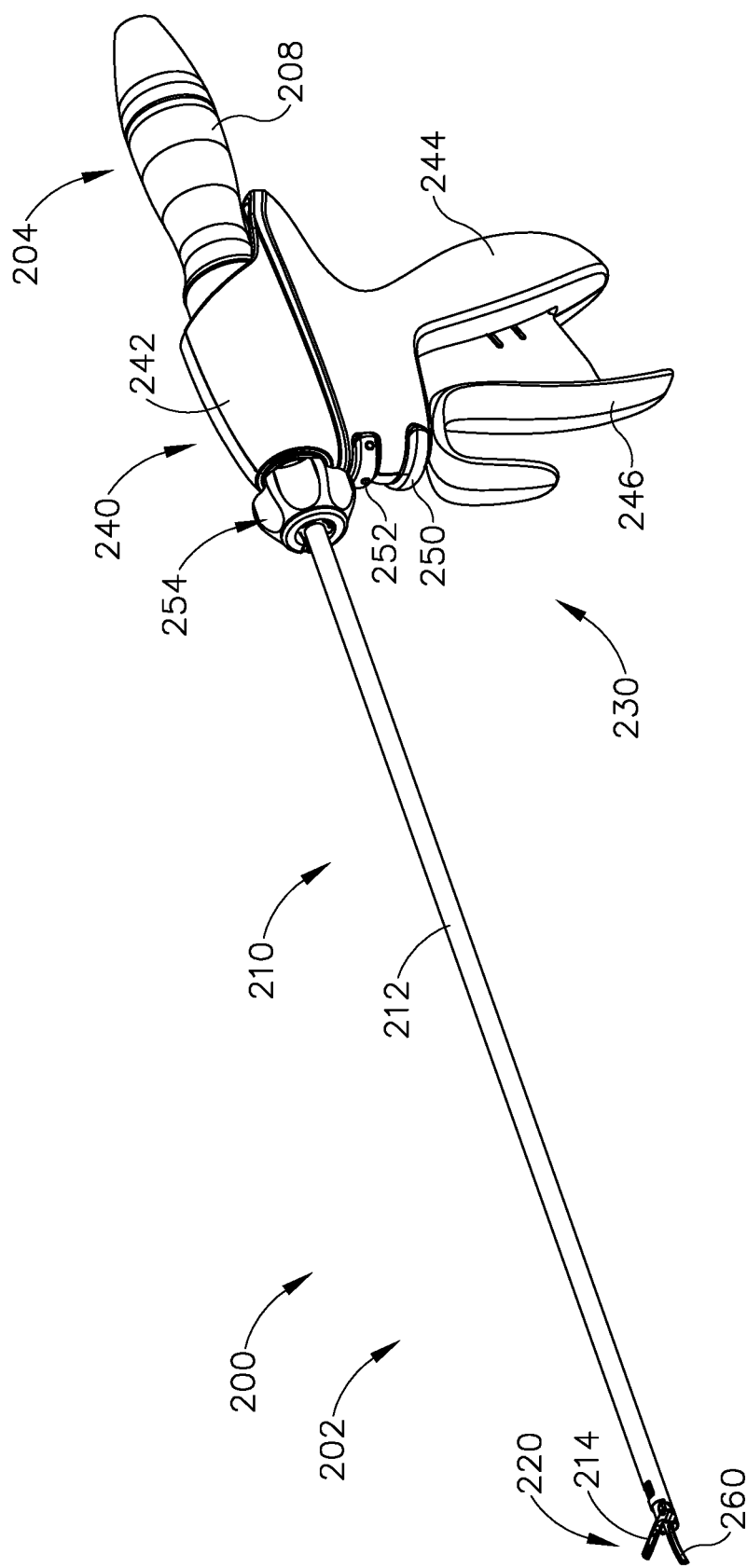
FIG. 2 depicts a perspective view of a second exemplary ultrasonic surgical instrument having a handle assembly, a shaft assembly, and an end effector.
Figure 3:
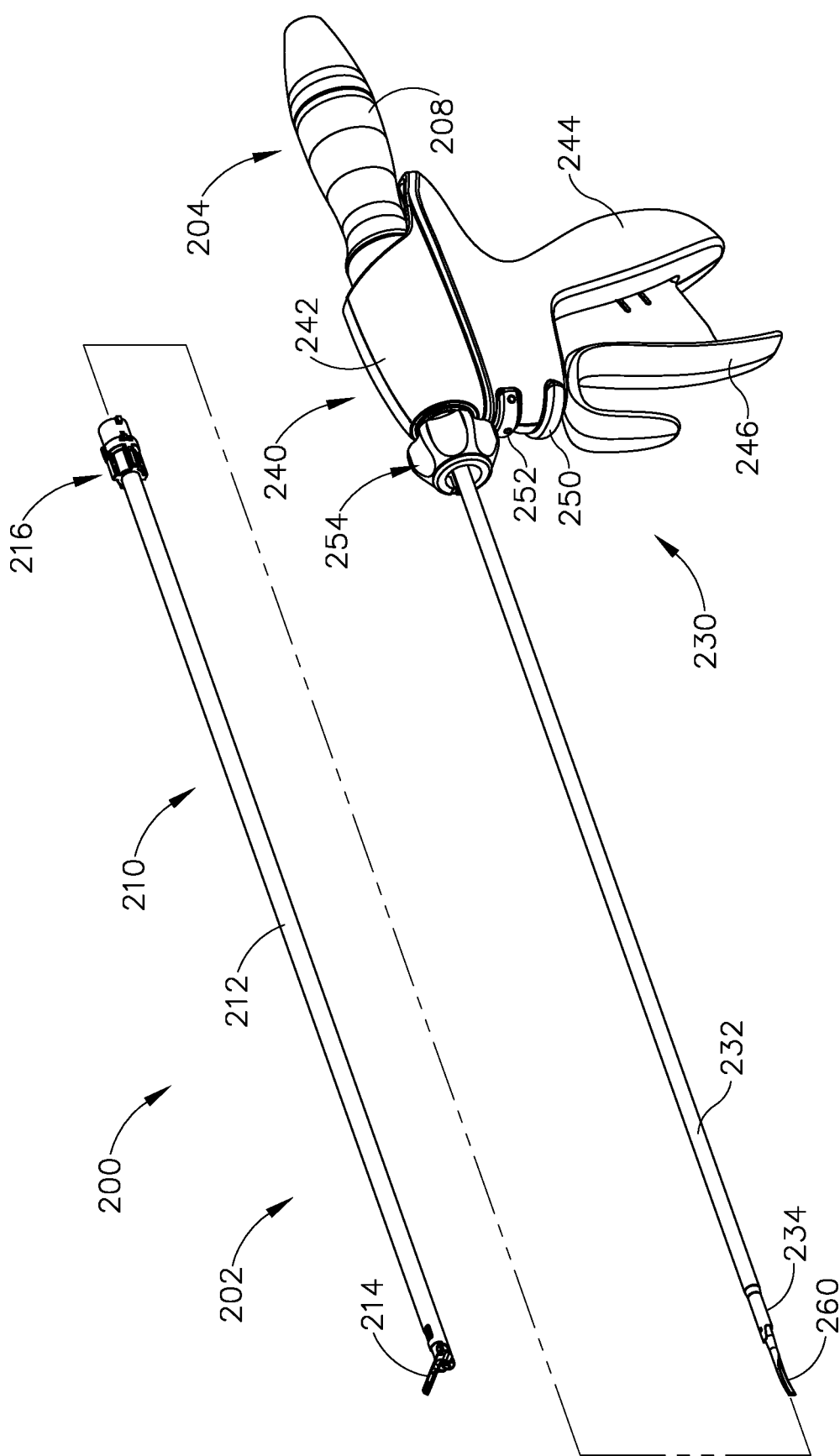
FIG. 3 depicts a perspective view of the ultrasonic surgical instrument of FIG. 2, but showing a disposable portion separated from a reusable portion.
Figure 4:
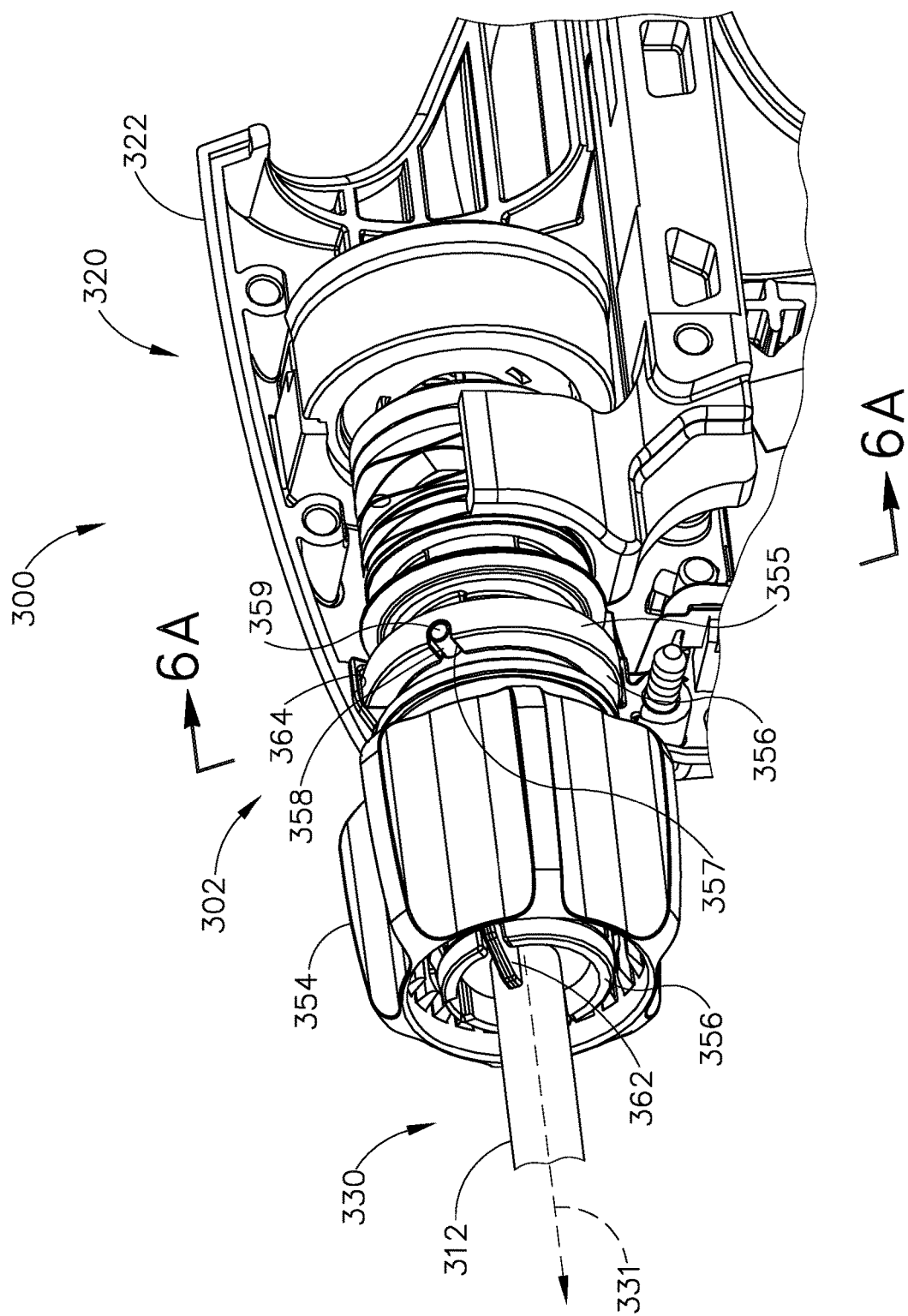
FIG. 4 depicts an enlarged, perspective view of a third exemplary ultrasonic surgical instrument, which may be used with a variation of the disposable portion of the ultrasonic surgical instrument of FIG. 3, and shown with a housing shroud removed for greater clarity.

FIGS. 2-3 show an exemplary variation of instrument (100) in the form of ultrasonic surgical instrument (200). Except as otherwise described below, ultrasonic surgical instrument (200) may be configured and operable just like instrument (100) described above and/or in accordance with any of the various teachings of the various patent references cited herein. Surgical instrument (200) is configured to be readily broken down into disposable and reusable components. In particular, surgical instrument (200) of this example comprises a reusable assembly (204) and a partially disposable assembly (202). When fully assembled, surgical instrument (200) provides an end effector (220) that includes an ultrasonic blade (260) and a clamp arm (214), which is pivotable toward and away from ultrasonic blade (260). End effector (220) is thus operable to grasp, ultrasonically seal, and ultrasonically sever tissue as described herein and as described in various references cited herein.

Reusable assembly (204) comprises an ultrasonic transducer (208), which is operable to convert electrical power into ultrasonic vibrations, also as described herein and as described in various references cited herein. Ultrasonic transducer (208) is acoustically coupled with ultrasonic blade (260) via an acoustic waveguide (234), a portion of which is shown in FIG. 3. It should be understood that ultrasonic transducer (208), ultrasonic blade (260), and acoustic waveguide (234) may be configured in accordance with the teachings of any of the various references cited herein; or in any other suitable fashion.

Shaft assembly, or partially disposable assembly (202), of the present example comprises a disposable sub-assembly (210) and a reusable sub-assembly (230). Sub-assemblies (210, 230) are configured to be coupled together to form partially disposable assembly (202), which may then be coupled with reusable assembly (204) for form a complete ultrasonic surgical instrument (200). As shown in FIG. 3, disposable sub-assembly (210) comprises an outer tube (212). Clamp arm (214) is pivotally coupled with a distally projecting tongue of outer tube (212). A coupling member (216) is fixedly secured to the proximal end of outer tube (212). Disposable sub-assembly (210) further comprises a distal inner tube member (not shown), which is slidably and coaxially disposed within the distal end of outer tube (212). This distal inner tube member is also pivotally coupled with clamp arm (214) via a distally projecting tongue of the distal inner tube member. Thus, when outer tube (212) translates longitudinally relative to the distal inner tube member, clamp arm (214) will pivot toward and away from ultrasonic blade (260).

Reusable sub-assembly (230) of the present example comprises a handle assembly (240), a proximal inner tube (232), acoustic waveguide (234), and ultrasonic blade (260). Proximal inner tube (232) is configured to removably couple with the distal inner tube member (not shown) of disposable sub-assembly (210) first when sub-assemblies (210, 230) are assembled together. When proximal inner tube (232) is coupled with the distal inner tube member (not shown) of disposable sub-assembly (210), inner tube (232) remains longitudinally stationary relative to handle assembly (240).

Body, such as handle assembly (240), comprises a housing (242) that defines a pistol grip (244). Handle assembly (240) further includes a clamp actuator (246) that is pivotable toward and away from pistol grip (244); and a pair of buttons (250, 252). Buttons (250, 252) are operable to activate ultrasonic transducer (208) to thereby activate ultrasonic blade (260). In particular, one button (250) will provide activation of ultrasonic blade (260) at one power level or profile; while the other button (252) will provide activation of ultrasonic blade (260) at another power level or profile. Of course, any other suitable user input feature(s) may be used. It should also be understood that handle assembly (240) may be modified to include a feature that is operable to activate RF electrosurgical energy at end effector (220) (e.g., like button (125) described above).

Clamp actuator (246) is operable to actuate clamp arm (214), such that clamp arm (214) will pivot toward ultrasonic blade (260) when clamp actuator (246) us pivoted toward pistol grip (244); and such that clamp arm (214) will pivot away from ultrasonic blade (260) when clamp actuator (246) us pivoted away from pistol grip (244). In the present example, this movement is provided by translating outer tube (212) longitudinally relative to housing (242) in response to pivotal movement of clamp actuator (246), while inner tube (232) remain longitudinally stationary relative to housing (242). Various suitable ways in which outer tube (212) may be translated longitudinally in response to pivotal movement of clamp actuator (246) will be apparent to those of ordinary skill in the art in view of the teachings herein. It should also be understood that, in some alternative versions, clamp arm (214) is pivoted by translating inner tube (232) longitudinally relative to housing (242) while outer tube (212) remains longitudinally stationary relative to housing (242).

As shown in FIGS. 2-3, handle assembly (240) of the present example further includes a rotation knob (254). Rotation knob (254) is rotatable relative to housing (242). When instrument (200) is fully assembled, rotation knob (254) is coupled with acoustic waveguide (234), inner tube (232), and outer tube (212) such that these components will rotate together collectively relative to housing (242). Rotation knob (254) also provides guidance to disposable sub-assembly (210) when disposable sub-assembly (210) is being coupled with reusable sub-assembly (230). By way of example only, rotation knob (254) may be configured and operable in accordance with the teachings of any of the various references cited herein.

After ultrasonic surgical instrument (200) is used in a surgical procedure, reusable assembly (204) may be removed from partially disposable assembly (202). After reusable assembly (204) is removed from partially disposable assembly (202), disposable sub-assembly (210) is then be removed from reusable sub-assembly (230) Reusable assembly (204), disposable sub-assembly (210), and reusable sub-assembly (230) may then be subject to different kinds of processing. Examples of such subsequent processing are described below, while other examples will be apparent to those of ordinary skill in the art in view of the teachings herein.

In some instances, reusable assembly (204) may be cleaned, sterilized, and re-used up to 100 times (by way of example only). Disposable sub-assembly (210) may be disposed of immediately, such that disposable sub-assembly (210) is only used in one single surgical procedure. Reusable sub-assembly (230) may be cleaned, sterilized, and re-used in different surgical procedures between 2 to 20 times (by way of example only). Of course, these re-use scenarios are merely illustrative examples. It should nevertheless be understood that the configuration of partially disposable assembly (202) may minimize the amount of single-use material that is disposed of after each surgical procedure. It should also be understood that, in some variations, partially disposable assembly (202) is simply disposed of as a single unit. In other words, in some variations, partially disposable assembly (202) is not configured to be disassembled into disposable sub-assembly (210) and reusable sub-assembly (230).

By way of example only, as part of the post-surgery processing for re-use, reusable assembly (204) and/or reusable sub-assembly (230) may be sterilized in a conventional relatively low temperature, relatively low pressure, hydrogen peroxide sterilization process (e.g., in a STERRAD® sterilizing system by Advanced Sterilization Products of Irvine, Calif.). Alternatively, reusable assembly (204) and/or reusable sub-assembly (230) may be sterilized using any other suitable systems and techniques.

In addition to the foregoing, instrument (200) may be constructed and operable in accordance with at least some of the teachings of U.S. patent application Ser. No. 15/270,540, entitled "Ultrasonic Surgical Instrument with Removable Shaft Assembly Portion," filed Sep. 20, 2016, issued as U.S. Pat. No. 10,327,797 on Jun. 25, 2019, the disclosure of which is incorporated by reference herein; and/or U.S. patent application Ser. No. 15/270,600, entitled "Ultrasonic Surgical Instrument with Removable Shaft Assembly Portion," filed Sep. 20, 2016, issued as U.S. Pat. No. 10,492,820 on Dec. 3, 2019, the disclosure of which is incorporated by reference herein. In addition, or in the alternative, instrument (200) may be constructed and operable in accordance with at least some of the teachings of any of the various patent references cited herein.

III. Exemplary Shaft Assembly Rotation Systems

As described above, one or more instruments (100, 200) include a rotation knob (154, 254) which is rotatable relative to housing (122, 242). In one example, when instrument (200) is fully assembled, rotation knob (254) is coupled with acoustic waveguide (234), inner tube (232), and outer tube (212) such that these components will rotate together collectively relative to housing (242). While such rotation may be desirable in some instances, connecting acoustic waveguide (234) to surrounding structures, such as inner tube (232) and outer tube (212), for rotation tends to generate friction at couplings to acoustic waveguide (234) as acoustic waveguide (234) vibrates with ultrasonic frequencies driven by an ultrasonic generator, such as generator (116). In turn, this friction causes premature wear at couplings and associated joints with acoustic waveguide (234) and may result in damage or even premature failure of one or more portions of instruments (100, 200) due to use. It may thus be desirable to provide instruments (100, 200) with couplings to acoustic waveguide (234) that allow for rotation of shaft assembly (130, 202) relative to housing (122, 242) and inhibit such premature wear from ultrasonic vibrations of acoustic waveguide (234).

Various examples of ultrasonic surgical instruments (300, 400) described below provide various structures and techniques through which a shaft assembly and end effector may be rotated about a longitudinal axis defined by a centerline of the shaft assembly, such as shaft assembly (130, 202) and end effector (140, 220), while reducing wear about acoustic waveguide (234). By having the ability to rotate these components, the operator of ultrasonic surgical instruments (100, 200, 300, 400) is provided with greater flexibility to maneuver end effector (140, 220) to various positions as may be required by each individual surgical circumstance with increased longevity of use and less component failures. One or more portions of such shaft assembly rotation systems associates with ultrasonic surgical instruments (300, 400), discussed below, may thus be incorporated, in whole or in part, in instrument (100, 200) as desired. While various examples of features configured to rotate shaft assembly (130, 202) will be described in greater detail below, other examples will be apparent to those of ordinary skill in the art according to the teachings herein.

A. Exemplary Shaft Assembly Rotation System with Guide Pin

FIGS. 4-10 illustrate a third exemplary ultrasonic instrument (300), which comprises various components and features similar to instruments (100, 200). Particularly, instrument (300) comprises a body, such as a handle assembly (320) having a housing (322), and a shaft assembly (330). With respect to FIGS. 4-5, shaft assembly (330) further includes an inner tube (334) (see FIG. 6A) surrounding an acoustic waveguide (332) which is coupled at a first end to an ultrasonic transducer assembly (not shown) and at a second end to an ultrasonic blade (not shown), each of which may be respectively similar to ultrasonic transducer assembly (112, 208) (see FIGS. 1 and 2) and ultrasonic blade (160, 260) (see FIGS. 1 and 2) discussed above. Shaft assembly (330) also includes outer tube (312) surrounding inner tube (see FIG. 6A). During use of instrument (300), operator may selectively rotate shaft assembly (330) about a longitudinal axis (331) defined by the centerline of shaft assembly (330) to effectively rotate shaft assembly (330) about longitudinal axis (331).

To effect rotation of shaft assembly (330), instrument (300) includes a shaft assembly rotation system (302). Shaft assembly rotation system (302) is comprised of a rotation knob (354), an inner rotation knob driver (356), and a first example of a guide pin (358), whereby shaft assembly rotation system (302) is operatively coupled to shaft assembly (330). In this example, shaft assembly rotation system (302) is coupled directly to acoustic waveguide (332). Rotation knob (354), inner rotation knob driver (356), and guide pin (358) are operatively coupled together such that a rotation of rotation knob (354) about longitudinal axis (331) contacts and thereby communicates rotational torque to inner rotation knob driver (356) about longitudinal axis (331), which then contacts and thereby translates rotational torque to guide pin (358) about longitudinal axis (331).

In some examples, shaft assembly rotation system (302) further comprises one or more of a coupling feature (362) and a torque clip (not shown), each operatively coupled to rotation knob (354), inner rotation knob driver (356), and guide pin (358). For example, the torque clip (not shown) connects to the inner surface of rotation knob (354) to translate the rotational force from rotation knob (354) to inner rotation knob driver (356). Coupling feature (362) is included in shaft assembly rotation system (302) and configured to secure assembly of the various components to housing (322), wherein each also rotates about longitudinal axis (331) upon rotation of rotation knob (354).

Guide pin (358) comprises a cylindrical body shape having a first end (359) which mates with a first notch (357) in inner rotation knob driver (356) to effect the rotation. A second notch (357) is included in inner rotation knob driver (356) angularly opposite from first notch (357) and adapted to mate with a second end (361) (see FIG. 6A) of guide pin (358). As shaft assembly rotation system (302) rotates, first end (359) of guide pin (358) and a distal edge (355) of inner rotation knob driver (356) form a flush surface which moves through a rotational drive channel (364) defined by an inner surface of housing (322). Rotational drive channel (364) is thereby configured and adapted to receive and guide throughout 360-degree rotation at least one of inner rotation knob driver (356) and/or guide pin (358). In some examples, only ends (359, 361) of guide pin (358) extend into rotational drive channel (364), while in other examples, both ends (359, 361) of guide pin (358) and distal edge (355) of inner rotation knob driver (356) extend into rotational drive channel (364).

Figure 5:
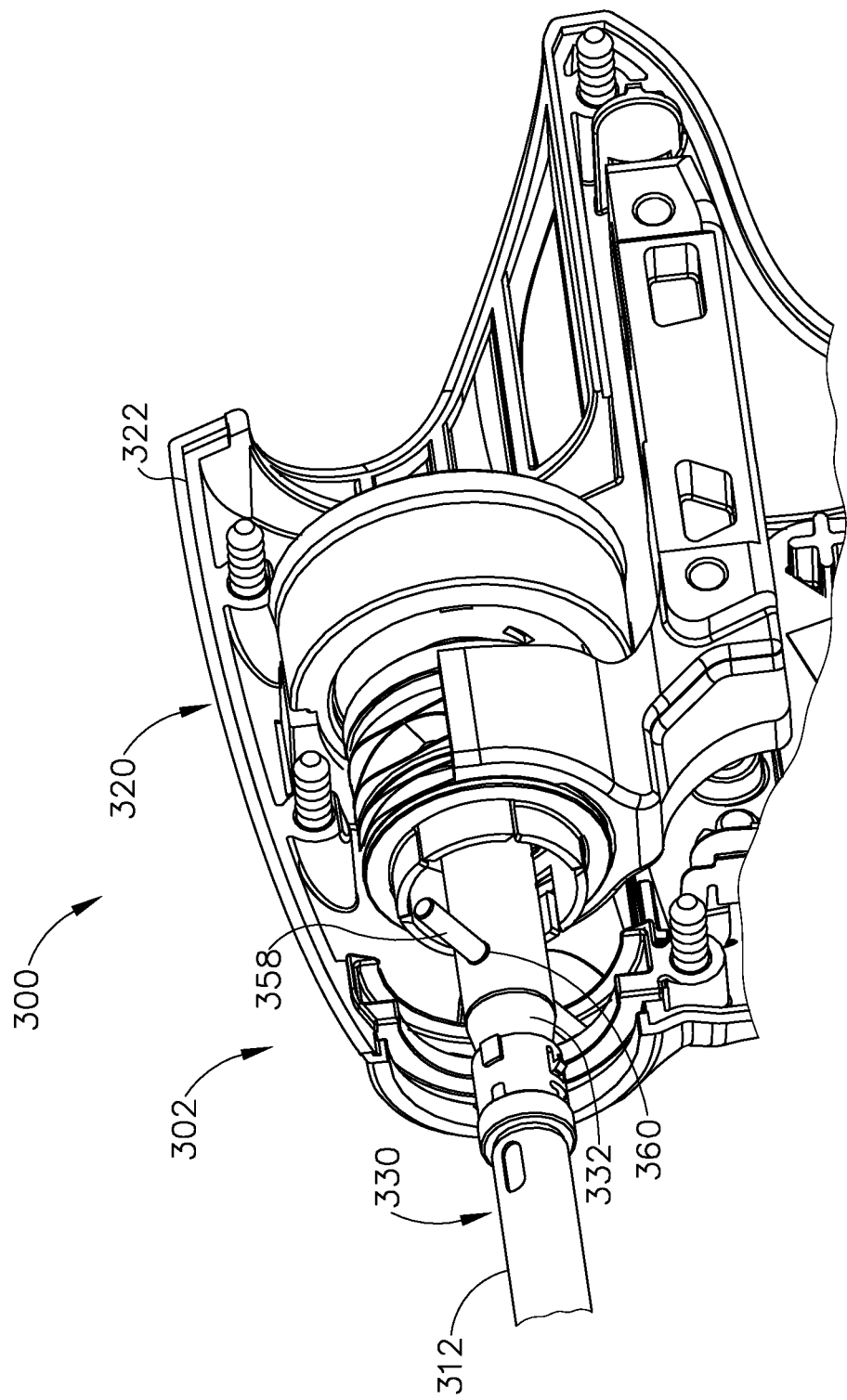
FIG. 5 depicts an enlarged, perspective view of the ultrasonic surgical instrument of FIG. 4 with a rotation knob, a torque clip, an inner rotation knob driver, and a coupling feature removed for greater clarity.

As illustrated in FIGS. 5 and 6A-6B, acoustic waveguide (332) includes a bore (360) configured to receive guide pin (358) to extend therethrough. As such, rotation of guide pin (358) urges rotation of acoustic waveguide (332) along with various other components of shaft assembly rotation system (302) operatively coupled to guide pin (358) and/or acoustic waveguide (332). As described above, acoustic waveguide (332) is configured to communicate ultrasonic vibration signals therealong, and bore (360) with guide pin (358) are positioned at a node of such vibrations for reducing movement of acoustic waveguide (332) to, in turn, reduce friction between guide pin (358) and any structure engaged with guide pin (358) to at least some extent.

As illustrated in FIGS. 6A-6B and in greater detail in FIGS. 7-8, guide pin (358) has a base layer (370) and an inner insulating layer (372) configured to insulate base layer (370). Base layer (370) is a metal material forming a solid core (373) and is therefore suited to withstand the torque forces required to secure various components to acoustic waveguide (332) (see FIG. 6A). Inner insulating layer (372) is a silicone material, or otherwise any similar material suitable for damping ultrasonic vibrations. Inner insulating layer (372) therefore forms an insulating layer between base layer (370) and the internal surface of bore (360) (see FIG. 6A) of acoustic waveguide (332) (see FIG. 6A) to damp ultrasonic vibrations and inhibit such vibrations from propagating through instrument (300) for reducing the likelihood of associated damage. Additionally, an outer insulating layer (374) is included on the exterior surface of guide pin (370). Outer insulating layer (374) is a heat shrink material configured to protect inner insulating layer (372) from wear by creating an insulation barrier between acoustic waveguide (332) (see FIG. 6A) and inner tube (334) (see FIG. 6A). Outer insulating layer (374) inhibits metal-on-metal contact to further reduce the likelihood of wear and associated damage.

In the present example, guide pin (358) has core (373) with a shallow annular groove (375a) and a deep annular groove (375b) within shallow annular groove (375a), each of which extends along the length of core (373) between ends (359, 361) and centered therebetween. Inner insulating layer (372) is positioned within deep annular groove (375b) and concentrated around the center of base layer (370) adjacent to where guide pin (358) contacts bore (360) (see FIG. 6A) of acoustic waveguide (332) (see FIG. 6A). Outer insulating layer (374) is positioned within shallow annular groove (375a) also concentrated around the center of base layer (370) to cover inner insulating layer (372) for inhibiting contact as discussed above. Base layer (370) is therefore exposed near ends (359, 361) of guide pin (358), whereas layers (374, 370) are nested within an outer envelope of core (373).

FIGS. 9-10 show a second example of a guide pin (358') having another exemplary insulating configuration. In the present example, guide pin (358') has an inner insulating layer (372') and an outer insulating layer (374') on a core (373') between a pair of ends (359', 361') similar to guide pin (358) (see FIG. 8) with like materials discussed above, but with a differing structural arrangement. Core (373') is cylindrical and free from grooves (375a, 375b) such that base layer (370') of core (373') is smooth. Inner insulating layer (372') radially surrounds base layer (370') and, in turn, outer insulating layer (374') radially surrounds inner insulating layer (372') about base layer (370') for inhibiting contact as discussed above. In the present example, base layer (370') remains exposed at ends (359') of guide pin (358'), but may also be covered by one or more layers (372', 374') in alternative examples.

B. Exemplary Shaft Assembly Rotation System with Wrench Driver

FIGS. 11-25B illustrate a fourth exemplary ultrasonic instrument (400) which comprises various components and features similar to instruments (100, 200, 300). Particularly, instrument (400) comprises a body, such as a handle assembly (420) having a housing (422), and a shaft assembly (430). Shaft assembly (430) further includes an inner tube (434) (see FIG. 16) surrounding an acoustic waveguide (432) (see FIG. 16), which is coupled at a first end to an ultrasonic transducer assembly (not shown) and at a second end to an ultrasonic blade (not shown), each of which may be respectively similar to ultrasonic transducer assembly (112, 208) (see FIGS. 1 and 2) and ultrasonic blade (160, 260) (see FIGS. 1 and 2). Shaft assembly (430) also includes outer tube (412) surrounding inner tube (434) (see FIG. 16). During use of instrument (400), operator may selectively rotate shaft assembly (430) about a longitudinal axis (431) defined by the centerline of shaft assembly (430) to effectively rotate shaft assembly (430) about longitudinal axis (431).

Figure 11:
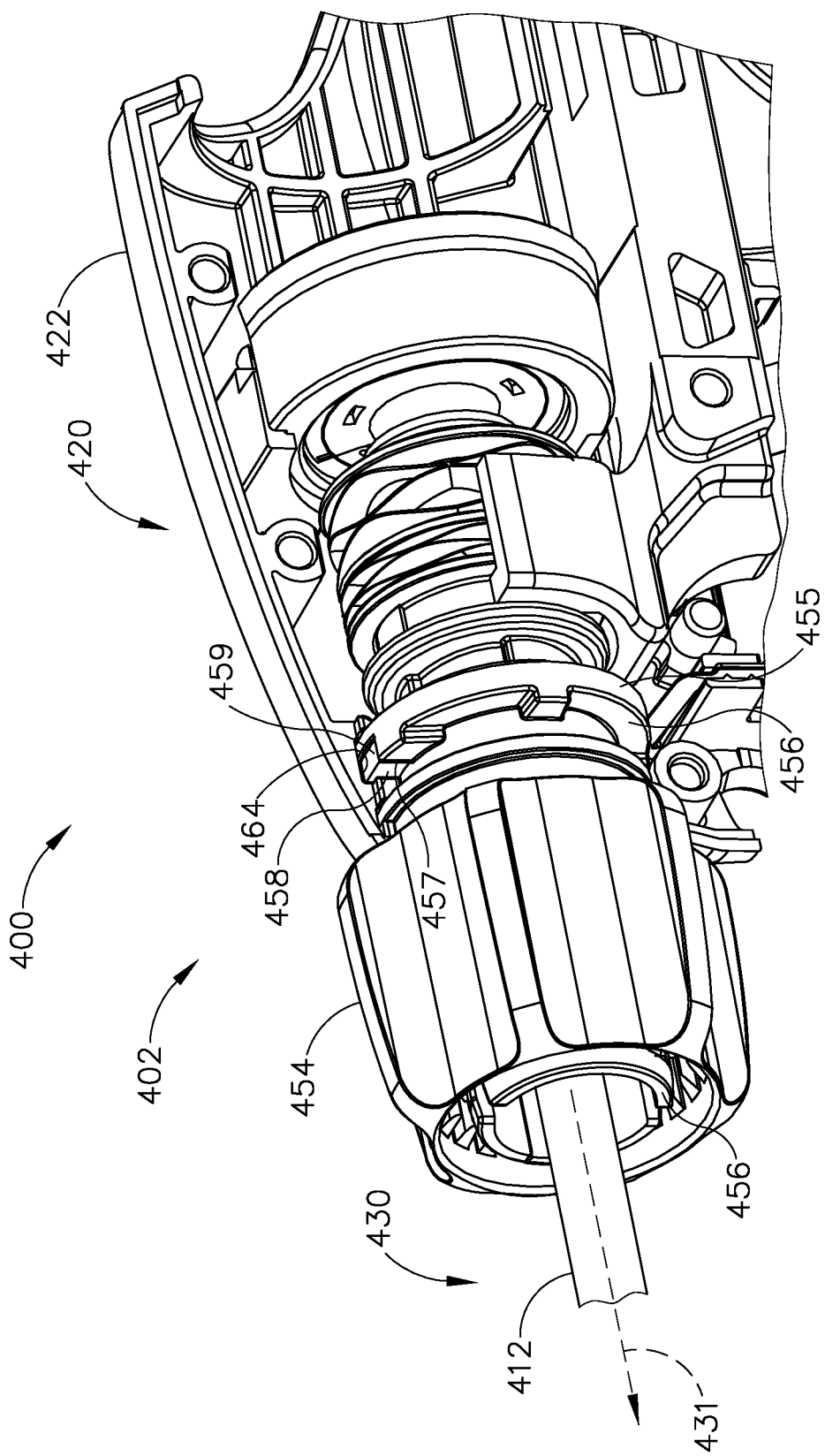
FIG. 11 depicts an enlarged, perspective view of a fourth exemplary ultrasonic surgical instrument, which may be used with a variation of the disposable portion of the ultrasonic surgical instrument of FIG. 3, and shown with a housing shroud removed for greater clarity.
Figure 12:
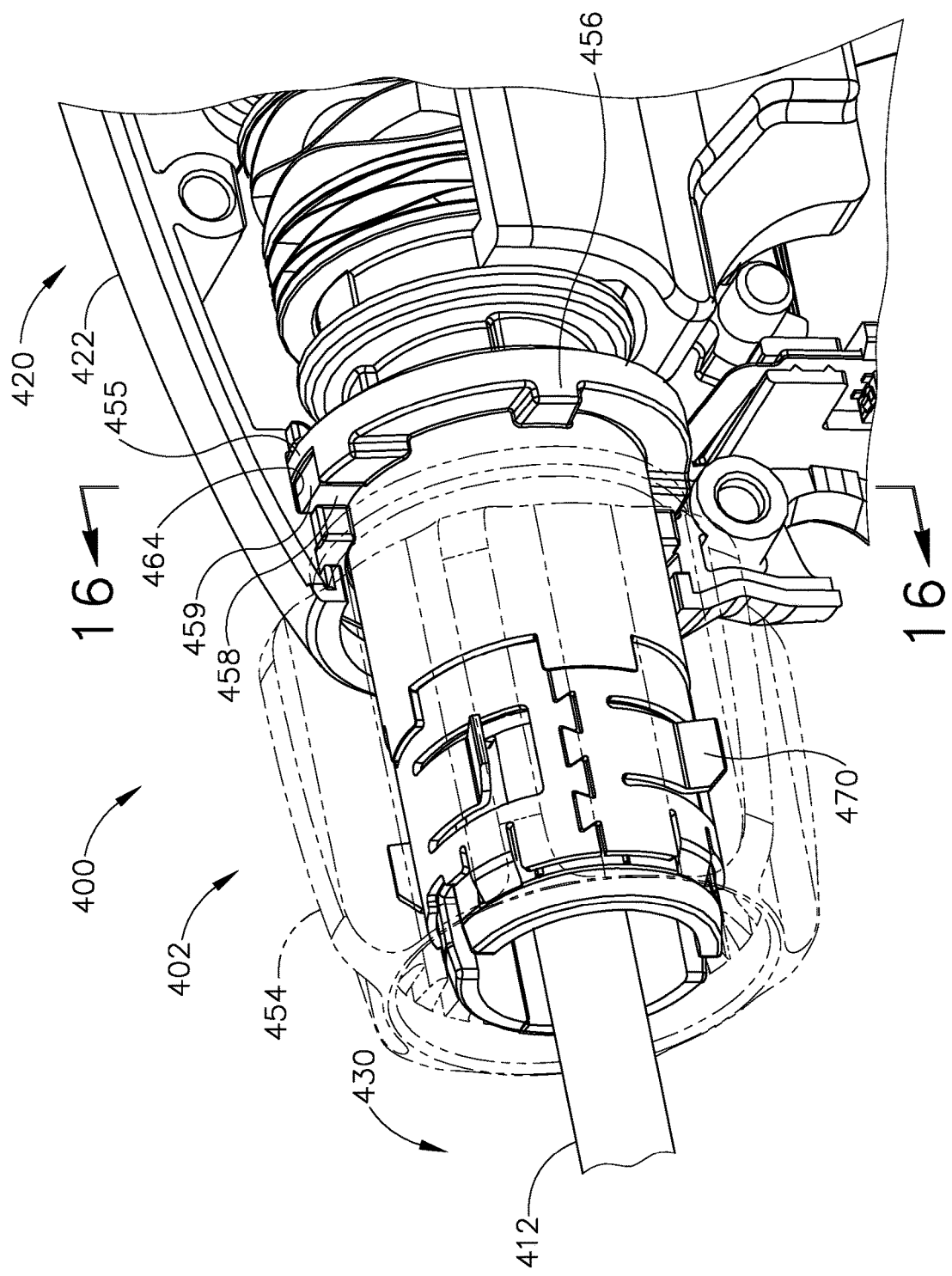
FIG. 12 depicts an enlarged, perspective view of the ultrasonic surgical instrument of FIG. 11 with a rotation knob hidden for greater clarity.
Figure 13:
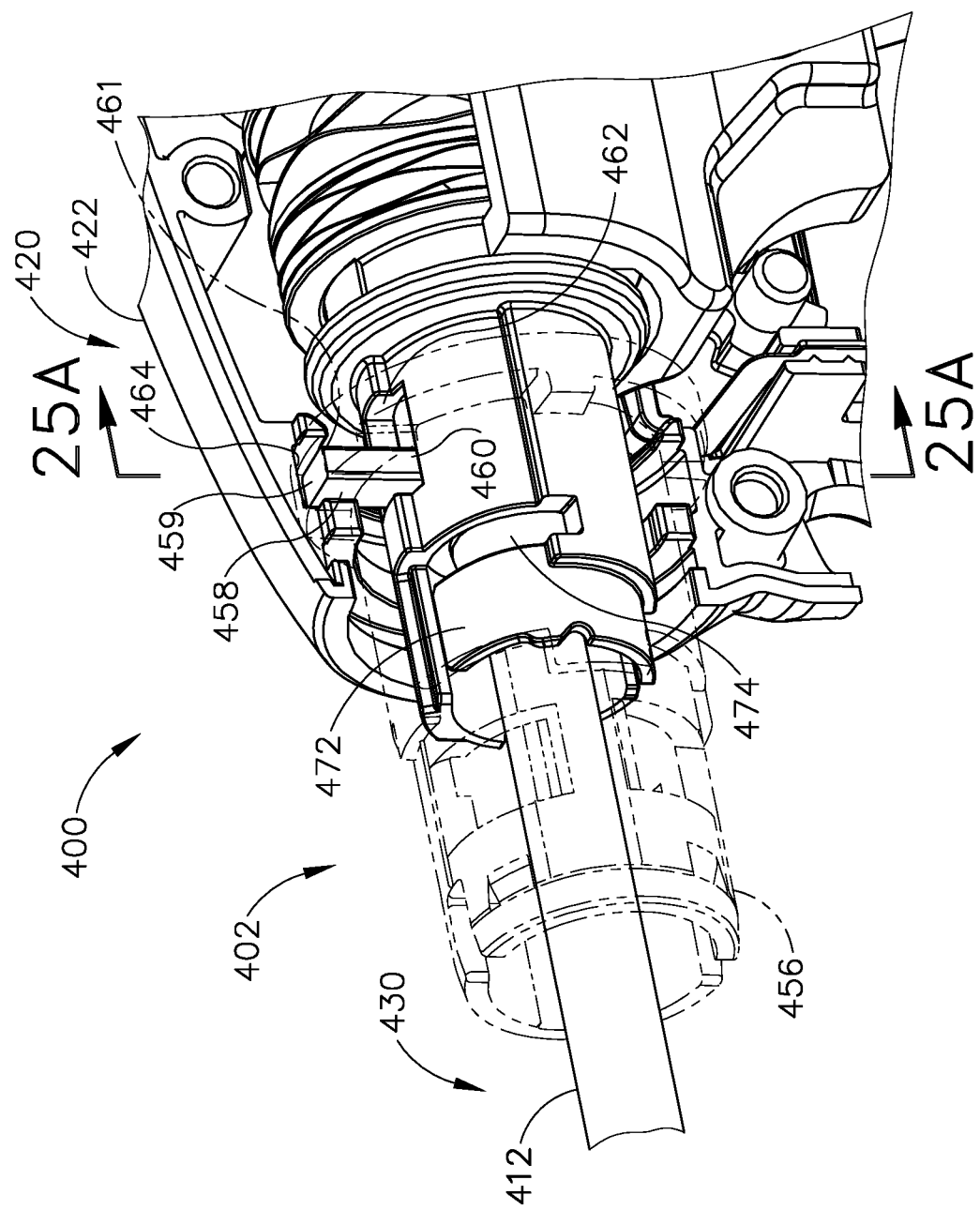
FIG. 13 depicts an enlarged, perspective view of the ultrasonic surgical instrument of FIG. 11 with the rotation knob and a torque clip removed and an inner rotation knob driver hidden for greater clarity.

To effect rotation of shaft assembly (430), with reference to FIGS. 11-13, instrument (400) includes a shaft assembly rotation system (402). Shaft assembly rotation system (402) is comprised of at least a rotation knob (454), an inner rotation knob driver (456), a driver wrench (474), and a rotational driver (458). In this example, shaft assembly rotation system (402) is engaged with acoustic waveguide (432) (see FIG. 15) such that acoustic waveguide (432) (see FIG. 15) is free from any holes extending radially into acoustic waveguide (432) (see FIG. 15), such as bore (360) (see FIG. 6A) discussed above in another example. Rotation knob (454), inner rotation knob driver (456), driver wrench (474), and rotational driver (458) are operatively coupled together such that rotating rotation knob (454) about longitudinal axis (431) contacts and communicates rotational torque to inner rotation knob driver (456). Rotation knob driver (456) thereby contacts and communicates rotational torque to driver wrench (474), rotational driver (458), and acoustic waveguide (432) for collective rotation of shaft assembly (430).

In one example, shaft assembly rotation system (402) further includes a torque clip (470) and an outer tube bayonet (472) as shown in reference to FIG. 12 and FIG. 13, each operatively coupled to rotation knob (454), inner rotation knob driver (456), driver wrench (474), and rotational driver (458). In order to longitudinally secure shaft assembly rotation system (402) into housing (422) while allowing for rotation, inner rotation knob driver (456) has an annular distal edge (455) received within a rotational drive channel (464). Rotational driver (458) also radially extends into rotational drive channel (464). As shaft assembly rotation system (402) rotates, end (459) of rotational driver (458) and distal edge (455) of inner rotation knob driver (456) form a flush surface which moves through rotational drive channel (464). Rotational drive channel (454) is thereby configured and adapted to receive and guide the at least one of inner rotation knob driver (456) and/or rotational driver (458) throughout 360-degree rotation. In some examples, only end (459) of rotational driver (458) extends into rotational drive channel (454), while in other examples, both end (459) of rotational driver (458) and distal edge (455) of inner rotation knob driver (456) extend into rotational drive channel (454).

In order to rotate shaft assembly rotation system (402), torque clip (470) couples to the inner surface of rotation knob (454) to communicate torque from rotation knob (454) to inner rotation knob driver (456). In turn, inner rotation knob driver (456) further communicates torque to outer tube bayonet (472) coupled therewith. Outer tube bayonet (472) proximally extends to operatively connect with and rotate additional ultrasonic drive features, such as ultrasonic transducer assembly (112, 208) (see FIGS. 1 and 2).

Figure 14:
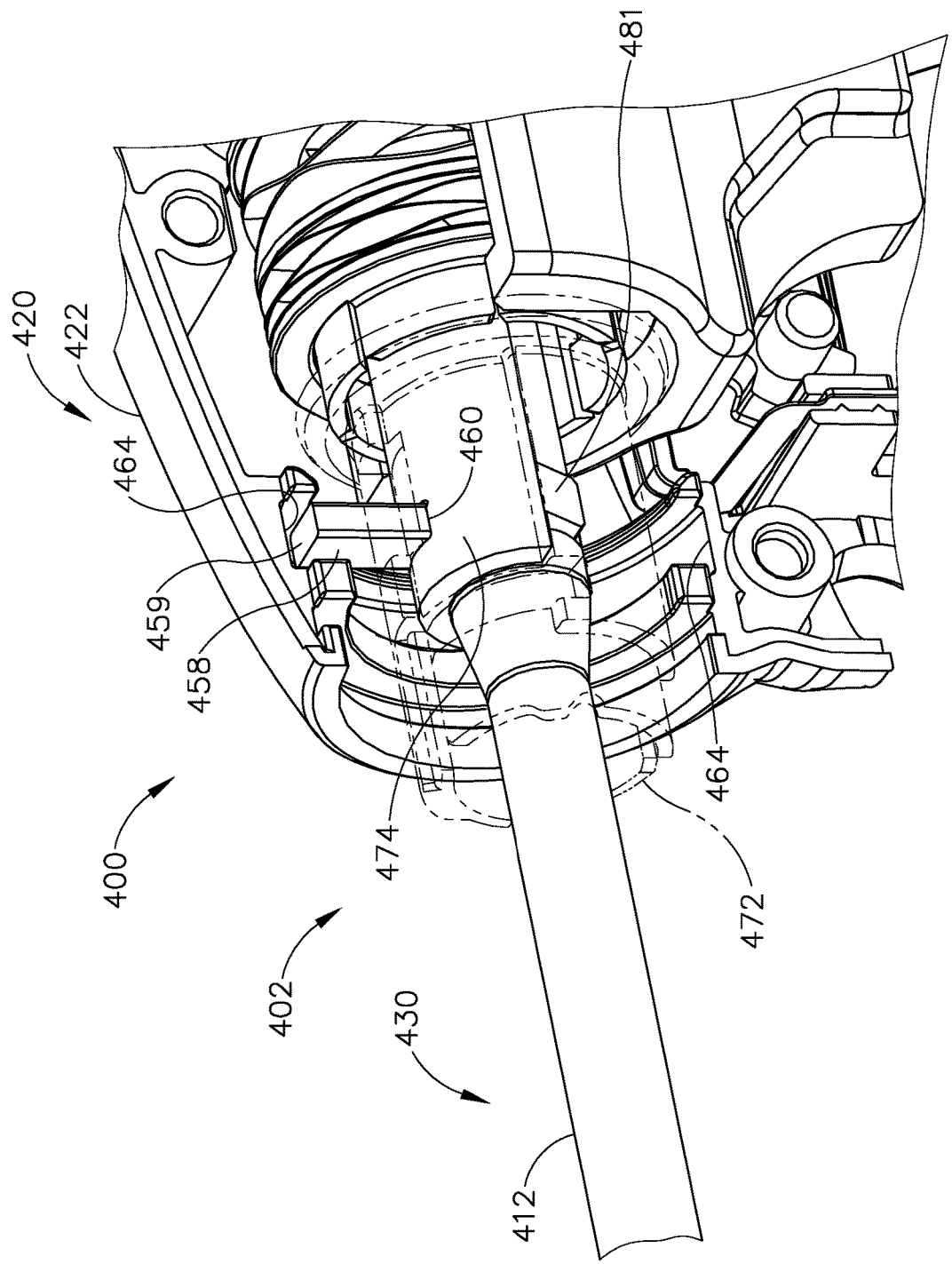
FIG. 14 depicts an enlarged, perspective view of the ultrasonic surgical instrument of FIG. 11 with the rotation knob, the torque clip, the inner rotation knob driver removed and an outer tube bayonet hidden for greater clarity.
Figure 15:
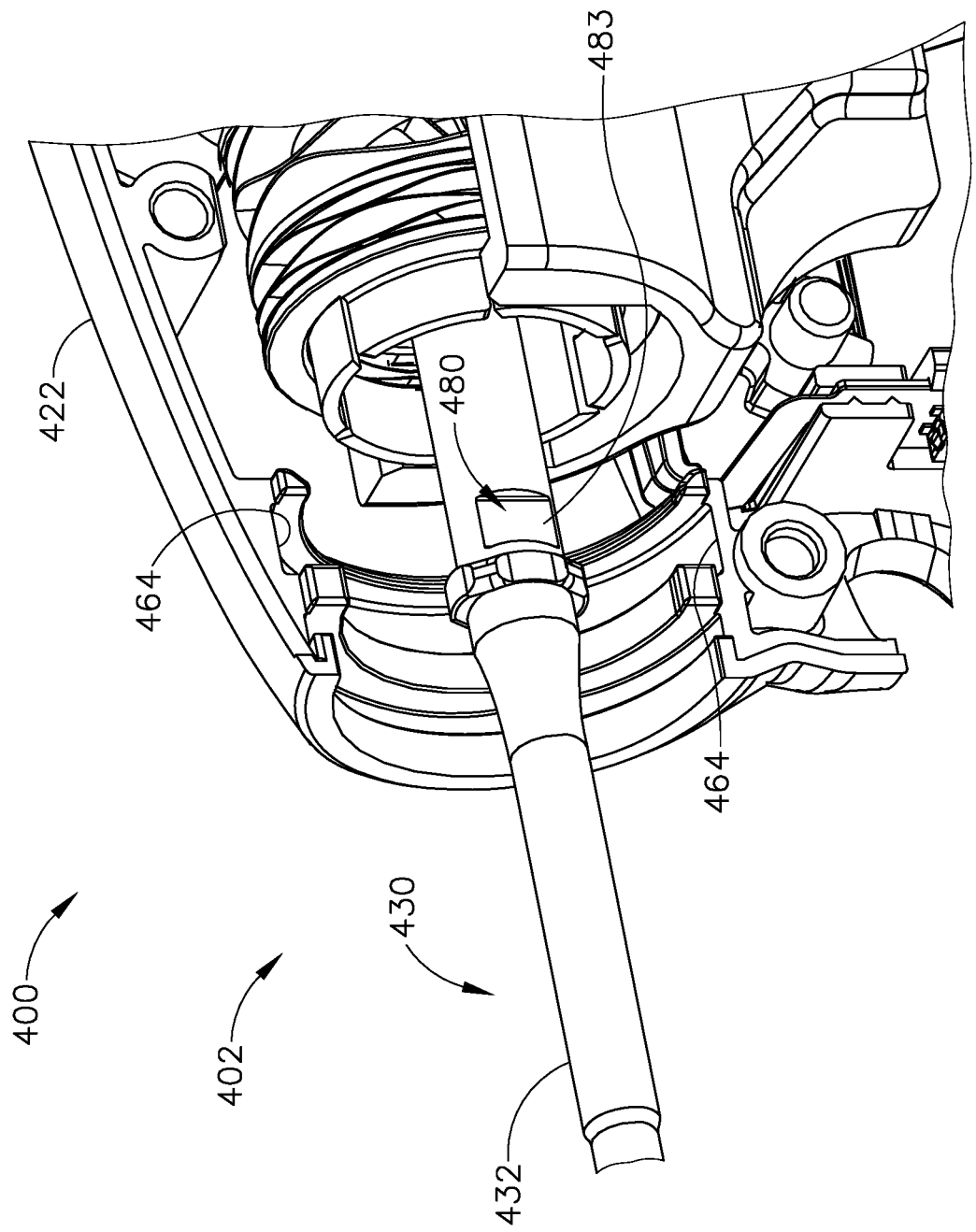
FIG. 15 depicts an enlarged, perspective view of the ultrasonic surgical instrument of FIG. 11 with the rotation knob, the torque clip, the inner rotation knob driver, the outer tube bayonet, a driver wrench, a rotational driver, an outer tube, and an inner tube removed for greater clarity.

In addition, inner rotation knob driver (456) also communicates torque to rotational driver (458) received within an opening (461) of inner rotation knob (456) shown in FIG. 13 and FIG. 14. Rotational driver (458) of the present example extends radially inward through an opening (462) in outer tube bayonet (472) to be received within and rotatably secure to driver wrench (474). Driver wrench (474) has a pair of keys (481) respectively engaged in a pair of notches (480) through acoustic waveguide (432) as shown in FIG. 14 and FIG. 15. Thus, keys (481) rotatably lock relative to notches (480) to grip and communicate torque to acoustic waveguide (432) without a hole extending into acoustic waveguide (432), such as radially through longitudinal axis (431). Notches (480) and keys (481) of the present example are positioned at a node of acoustic waveguide (432) to reduce vibration and friction generated between acoustic waveguide (432) and keys (481). Each component of shaft assembly rotation system (402) described herein is configured and adapted to couple directly to at least one other component of shaft assembly rotation system (402), such as in the order illustrated and described above. Of course, it will be appreciated that other such couplings between components may be similarly used such that the invention is not intended to be unnecessarily limited to the shaft assembly rotations system (402) described herein.

Figure 16:
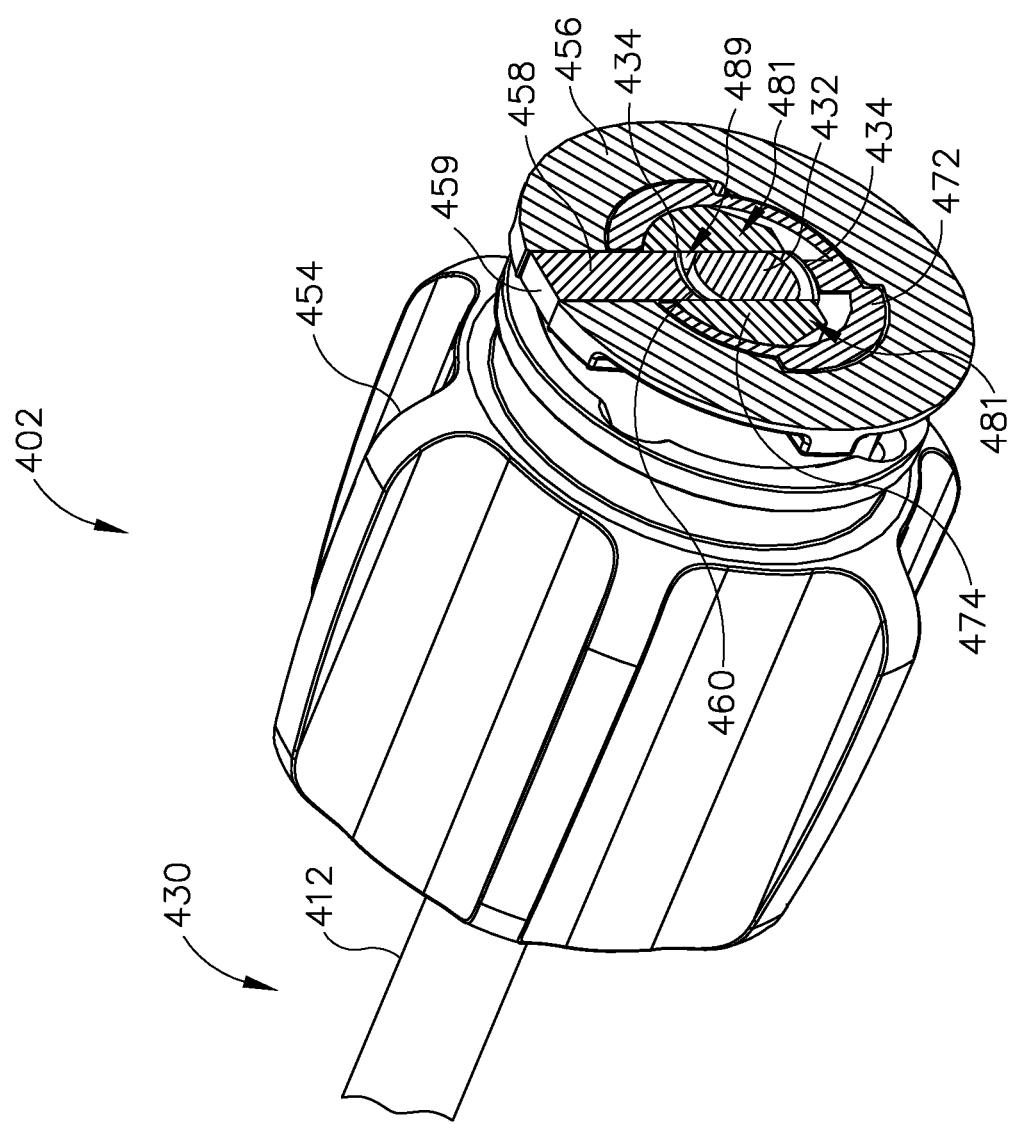
FIG. 16 depicts a sectional, perspective view of a shaft assembly rotation system of the ultrasonic surgical instrument of FIG. 11 taken along section line 16-16 of FIG. 12.
Figure 17:
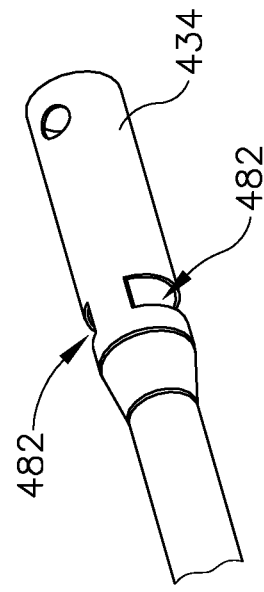
FIG. 17 depicts an enlarged, perspective view of an acoustic waveguide of the ultrasonic surgical instrument of FIG. 11.
Figure 18:
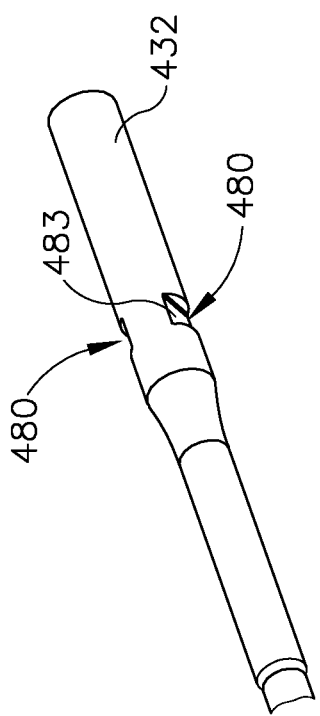
FIG. 18 depicts an enlarged, perspective view of the inner tube of the ultrasonic surgical instrument of FIG. 11.
Figure 19:
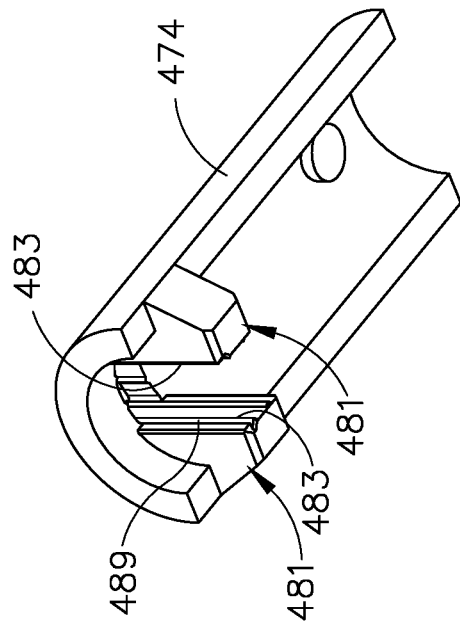
FIG. 19 depicts an upper perspective view of the driver wrench of the ultrasonic surgical instrument of FIG. 11.
Figure 20:
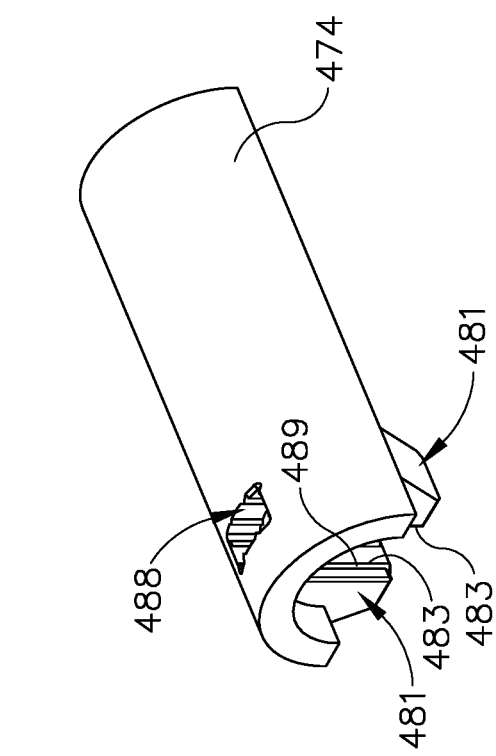
FIG. 20 depicts a lower perspective view of the driver wrench of the ultrasonic surgical instrument of FIG. 19.
Figure 21:
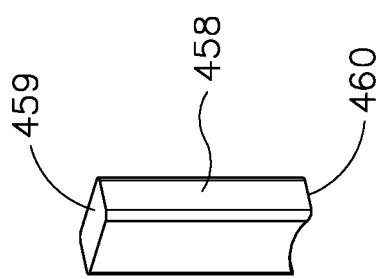
FIG. 21 depicts a perspective view of the rotational driver of the ultrasonic surgical instrument of FIG. 11.
Figure 23:
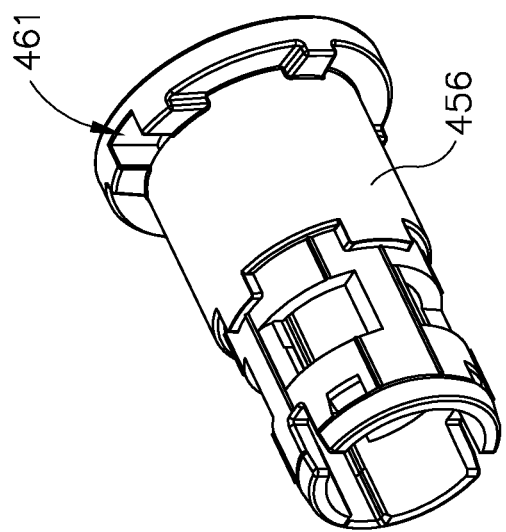
FIG. 23 depicts a perspective view of the inner rotation knob driver of the ultrasonic surgical instrument of FIG. 11.
Figure 22:
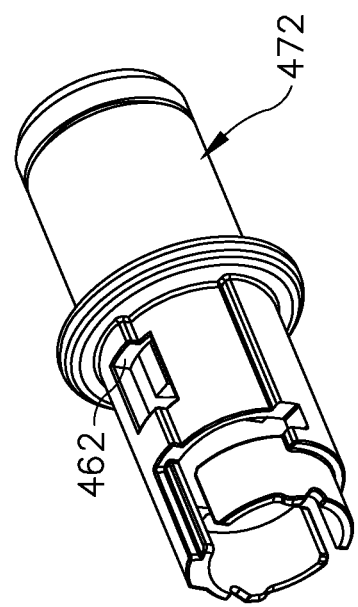
FIG. 22 depicts a perspective view of the outer tube bayonet of the ultrasonic surgical instrument of FIG. 11.

FIG. 16 shows that rotational driver (458) is effectively keyed to each of inner rotation knob driver (456), outer tube bayonet (472), and driver wrench (474), whereas FIGS. 17-24 show each component of shaft assembly rotation system (402) in greater detail. To this end, rotational driver (458) is inserted through opening (488) of driver wrench (474) whereby proximal end (460) of rotational driver (458) abuts inner tube (434) such that rotational driver (458) does not come into direct contact with acoustic waveguide (432) to effectuate rotation. Rather, driver wrench (474) is disposed around inner tube (434) with keys (481) respectively received in notches (480). Keys (481) and notches (480) have cooperatively engaging flats (483) to inhibit relative rotation therebetween. Keys (481) of the present example further include respective crush ribs (489) transversely extending along each flat (483) from opening (488) to the transverse terminal ends of keys (481). Crush ribs (489) deform upon engagement with flats (483) on acoustic waveguide (432) thereby reducing clearance, such as eliminating clearance, between keys (481) and acoustic waveguide (432) in order to reduce any rotational slip between keys (481) and acoustic waveguide (432) and more effectively grip acoustic waveguide (432). Such deformation of crush ribs (489) is resilient in the present example, but it will be appreciated that alternative deformation of crush ribs (489), such as a plastic deformation, for engagement between keys (481) and acoustic waveguide (432) may be so used. Such crush ribs (489) on keys (481) may similarly deform and engage rotational driver (458) for additional securement between rotational driver (458) and driver wrench (474). In addition, keys (481) of the present example extend respectively through a pair of angularly opposite openings (482) through inner tube (434) to allow for direct engagement between keys (481) and acoustic waveguide (432).

Figure 24:
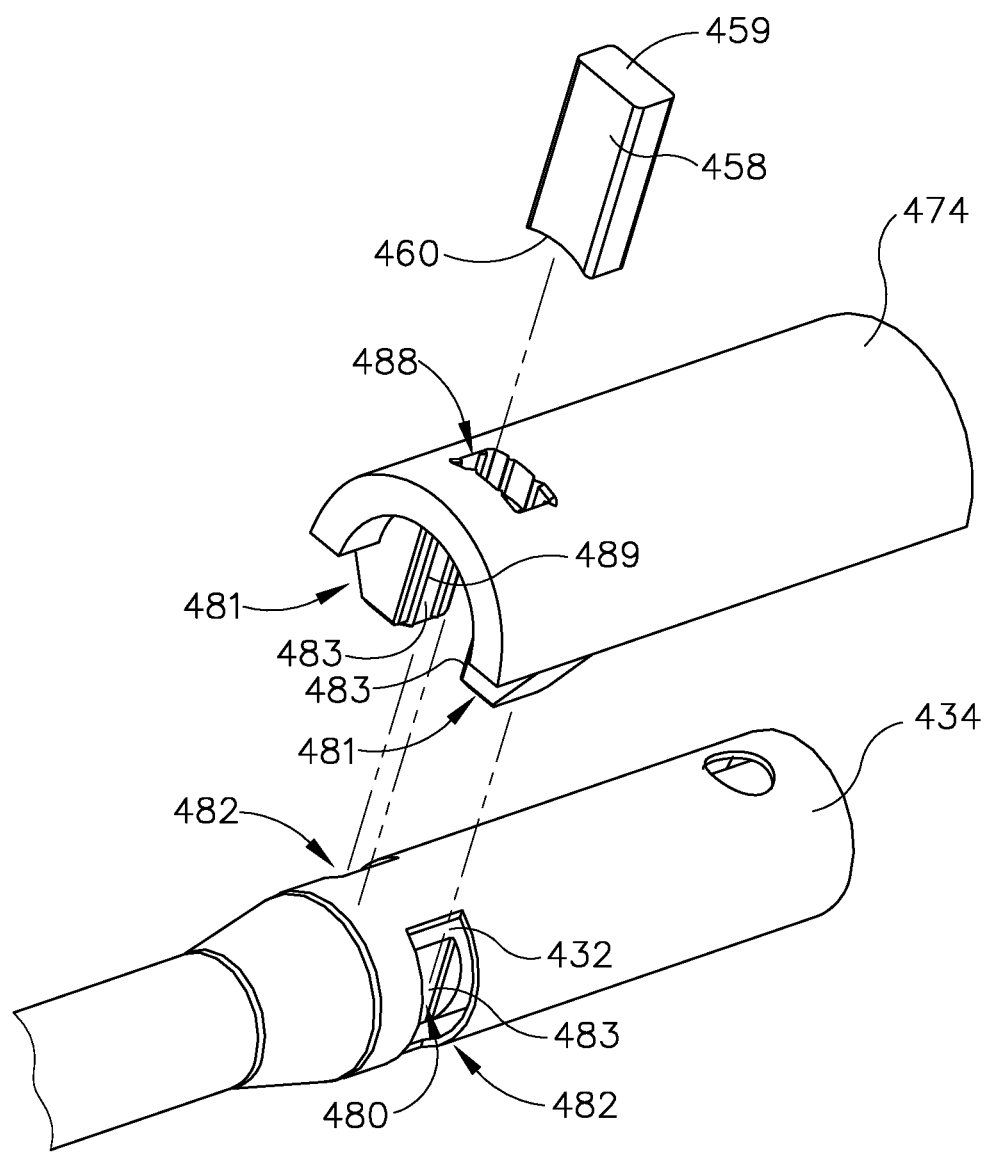
FIG. 24 depicts a partially exploded, perspective view of at least a portion of the shaft assembly rotation system of the ultrasonic surgical instrument of FIG. 11 including the acoustic waveguide, the inner tube, the driver wrench, and the rotational driver.
Figure 25B:
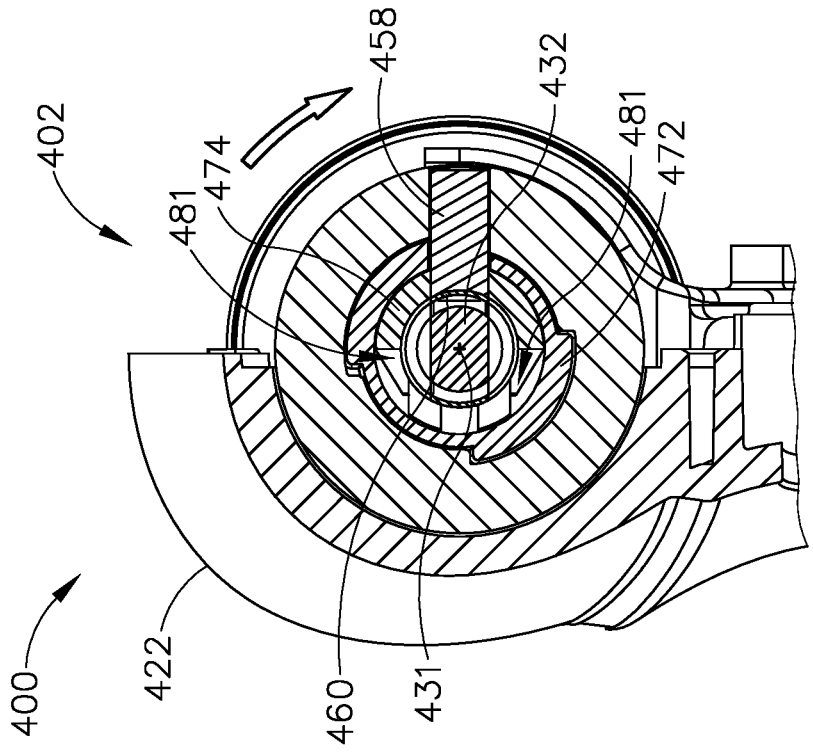
FIG. 25B depicts the enlarged, cross-sectional view of the shaft assembly rotation system similar to FIG. 25A, but showing the shaft assembly rotated from the first rotational position to a second rotational position.
Figure 25A:
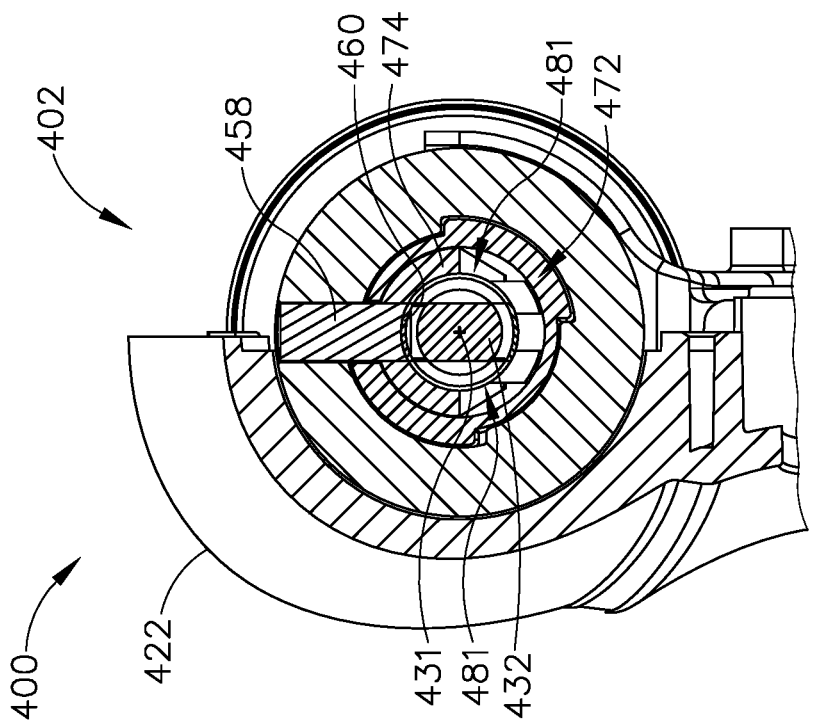
FIG. 25A depicts an enlarged, cross-sectional view of the shaft assembly rotation system of the ultrasonic surgical instrument of FIG. 11 taken along section line 25A-25A of FIG. 13, showing the shaft assembly rotated to a first rotational position.

With respect to FIGS. 24-25B, rotational driver (458) is inserted through opening (488) of driver wrench (474) such that proximal end (460) of rotational driver (458) rests against inner tube (434), while keys (481) of driver wrench (474) insert through openings (482) of inner tube (434) and mate into notches (480) of acoustic waveguide (432). By gripping rotation knob (454), the operator thereby directs rotation of rotation knob (454) as desired from a first rotational position to a second rotational position. In doing so, torque communicates from rotation knob (454) through rotational driver (458) to driver wrench (474) as discussed above in greater detail. Keys (481) for driver wrench (474) rotatably lock within notches (480) on acoustic waveguide (432) to thereby urge rotation of acoustic waveguide (432) about longitudinal axis (431) with a remainder of shaft assembly (430) relative to housing (422) of handle assembly (420) during use.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body including a rotational drive channel; (b) an end effector, including: (i) an ultrasonic blade, and (ii) a clamp arm movably coupled with the shaft assembly and distally extending therefrom; and (c) a shaft assembly extending between the body and the end effector defining a longitudinal axis and configured to rotatably couple to the body, the shaft assembly including: (i) an acoustic waveguide having a surface defining a first notch and acoustically coupled with the ultrasonic blade, (ii) a rotational driver configured to be received within the rotational drive channel, wherein the rotational driver is operable to rotate the shaft assembly relative to the body about the longitudinal axis, and (iii) a driver wrench operatively coupled between the rotational driver and the acoustic waveguide and defining a first key, wherein the first notch of the acoustic waveguide is configured to receive the first key of the driver wrench thereby rotatably locking the driver wrench relative to the acoustic waveguide for rotating the shaft assembly relative to the body about the longitudinal axis.

Example 2

The surgical instrument of Example 1, wherein the driver wrench defines a second key and the surface of the acoustic waveguide defines a second notch, and wherein the second notch is configured to receive the second key thereby further rotatably locking the driver wrench relative to the acoustic waveguide for rotating the shaft assembly relative to the body about the longitudinal axis.

Example 3

The surgical instrument of Example 2, wherein the second notch is positioned angularly opposite from the first notch about the longitudinal axis on the surface of the acoustic waveguide.

Example 4

The surgical instrument of any one or more of Examples 1 through 3, wherein the body further includes a handle assembly having a clamp actuator operatively coupled to the clamp arm and configured to direct movement of the clamp arm relative to the ultrasonic blade.

Example 5

The surgical instrument of Example 4, wherein at least a portion of the shaft assembly is removably coupled relative to the handle assembly.

Example 6

The surgical instrument of Example 4, wherein at least one of the handle assembly or the body includes a knob configured to selectively rotate about the longitudinal axis, and wherein the knob is operatively connected to the rotational driver and configured to rotate the rotational driver about the longitudinal axis upon selective rotation thereof.

Example 7

The surgical instrument of Example 6, further comprising a torque clip connected between the knob and the rotational driver and configured to transmit torque from the knob to the rotational driver during rotation.

Example 8

The surgical instrument of any one or more of Examples 1 through 7, wherein the rotational driver is configured to fully rotate around the longitudinal axis within the rotational drive channel.

Example 9

The surgical instrument of any one or more of Examples 1 through 8, wherein the shaft assembly further includes: (i) an outer tube, and (ii) an inner tube positioned within the outer tube and configured to receive the acoustic waveguide positioned therethrough, wherein the outer tube and the inner tube are configured to translate relative to each other to move the clamp arm relative to the ultrasonic blade.

Example 10

The surgical instrument of Example 9, wherein the inner tube and the acoustic waveguide are secured to the body such that the outer tube is configured to translate relative to the inner tube, the acoustic waveguide, and the body.

Example 11

The surgical instrument of Example 9, wherein the inner tube has a first opening extending therethrough, and wherein the first key is configured to extend through the first opening of the inner tube adjacent to the first notch of the acoustic waveguide.

Example 12

The surgical instrument of Example 11, wherein the driver wrench is disposed around the inner tube.

Example 13

The surgical instrument of any one or more of Examples 9 through 12, wherein the inner tube has a second opening extending therethrough, wherein the driver wrench defines a second key and the surface of the acoustic waveguide defines a second notch, wherein the second notch is configured to receive the second key thereby further rotatably locking the driver wrench relative to the acoustic waveguide for rotating the shaft assembly relative to the body about the longitudinal axis, and wherein the second key is configured to extend through the second opening of the inner tube adjacent to the second notch of the acoustic waveguide.

Example 14

The surgical instrument of Example 13, wherein the second notch is positioned angularly opposite from the first notch about the longitudinal axis on the surface of the acoustic waveguide.

Example 15

The surgical instrument of any one or more of Examples 1 through 11, wherein the driver wrench is positioned between the rotational driver and the acoustic waveguide and thereby inhibits the rotational driver from direct contact with the acoustic waveguide.

Example 16

A surgical instrument, comprising: (a) a body; (b) an end effector, including: (i) an ultrasonic blade, and (ii) a clamp arm movably coupled with the shaft assembly and distally extending therefrom; and (c) a shaft assembly extending between the body and the end effector defining a longitudinal axis and configured to rotatably couple to the body, the shaft assembly, including: (i) an acoustic waveguide defining a first notch and a second notch, (ii) a rotational driver configured to rotate the shaft assembly relative to the body about the longitudinal axis, and (iii) a driver wrench operatively coupled to the rotational driver and the acoustic waveguide, wherein the driver wrench defines a first key and a second key, wherein the first and second keys are respectively received within the first and second notches thereby rotatably locking the driver wrench relative to the acoustic waveguide for rotating the shaft assembly relative to the body about the longitudinal axis.

Example 17

A surgical instrument, comprising: (a) a body including a rotational drive channel; (b) an end effector, including: (i) an ultrasonic blade, and (ii) a clamp arm movably coupled with the shaft assembly and distally extending therefrom; and (c) a shaft assembly extending between the body and the end effector defining a longitudinal axis and configured to rotatably couple to the body, the shaft assembly including: (i) an elongated tube, (ii) an acoustic waveguide positioned within the elongated tube and including a bore, and (iii) a guide pin positioned within the bore and configured to be received within the rotational drive channel, wherein the guide pin is configured to rotatably lock the elongated tube to the acoustic waveguide and longitudinally lock the acoustic waveguide to the body for rotating the shaft assembly relative to the body about the longitudinal axis.

Example 18

The surgical instrument of Example 17, wherein the guide pin includes a base layer and a first insulating layer configured to insulate the base layer.

Example 19

The surgical instrument of Example 18, wherein the base layer has a metal material forming a core, and wherein the first insulating layer has a silicone material.

Example 20

The surgical instrument of any one or more of Examples 18 through 19, wherein the guide pin includes a second insulating layer configured to insulate the first insulating layer, and wherein the second insulating layer has a heat shrink material.

V. Miscellaneous

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265, now abandoned; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body including a rotational drive channel;
   (b) an end effector, including:
      (i) an ultrasonic blade, and
      (ii) a clamp arm; and
   (c) a shaft assembly extending between the body and the end effector defining a longitudinal axis and configured to rotatably couple with the body, wherein the clamp arm is movably coupled with the shaft assembly and distally extending therefrom, the shaft assembly including:
      (i) an acoustic waveguide having a surface defining a first notch and acoustically coupled with the ultrasonic blade,
      (ii) a rotational driver configured to be received within the rotational drive channel, wherein the rotational driver is operable to rotate the shaft assembly relative to the body about the longitudinal axis, and
      (iii) a driver wrench operatively coupled between the rotational driver and the acoustic waveguide and defining a first key,
   wherein the first notch of the acoustic waveguide is configured to receive the first key of the driver wrench thereby rotatably locking the driver wrench relative to the acoustic waveguide for rotating the shaft assembly relative to the body about the longitudinal axis, wherein the first key is configured to translate in a direction perpendicular to the longitudinal axis to insert into the first notch.

2. The surgical instrument of claim 1, wherein the driver wrench defines a second key and the surface of the acoustic waveguide defines a second notch, and wherein the second notch is configured to receive the second key thereby further rotatably locking the driver wrench relative to the acoustic waveguide for rotating the shaft assembly relative to the body about the longitudinal axis.

3. The surgical instrument of claim 2, wherein the second notch is positioned angularly opposite from the first notch about the longitudinal axis on the surface of the acoustic waveguide.

4. The surgical instrument of claim 1, wherein the body further includes a handle assembly having a clamp actuator operatively coupled to the clamp arm and configured to direct movement of the clamp arm relative to the ultrasonic blade.

5. The surgical instrument of claim 4, wherein at least a portion of the shaft assembly is removably coupled relative to the handle assembly.

6. The surgical instrument of claim 4, wherein at least one of the handle assembly or the body includes a knob configured to selectively rotate about the longitudinal axis, and wherein the knob is operatively connected to the rotational driver and configured to rotate the rotational driver about the longitudinal axis upon selective rotation thereof.

7. The surgical instrument of claim 6, further comprising a torque clip connected between the knob and the rotational driver and configured to transmit torque from the knob to the rotational driver during rotation.

8. The surgical instrument of claim 1, wherein the rotational driver is configured to fully rotate around the longitudinal axis within the rotational drive channel.

9. The surgical instrument of claim 1, wherein the shaft assembly further includes:
   (i) an outer tube, and
   (ii) an inner tube positioned within the outer tube and configured to receive the acoustic waveguide positioned therethrough,
   wherein the outer tube and the inner tube are configured to translate relative to each other to move the clamp arm relative to the ultrasonic blade.

10. The surgical instrument of claim 9, wherein the inner tube and the acoustic waveguide are secured to the body such that the outer tube is configured to translate relative to the inner tube, the acoustic waveguide, and the body.

11. The surgical instrument of claim 9, wherein the inner tube has a first opening extending therethrough, and wherein the first key is configured to extend through the first opening of the inner tube adjacent to the first notch of the acoustic waveguide.

12. The surgical instrument of claim 11, wherein the driver wrench is disposed around the inner tube.

13. The surgical instrument of claim 12, wherein the inner tube has a second opening extending therethrough, wherein the driver wrench defines a second key and the surface of the acoustic waveguide defines a second notch, wherein the second notch is configured to receive the second key thereby further rotatably locking the driver wrench relative to the acoustic waveguide for rotating the shaft assembly relative to the body about the longitudinal axis, and wherein the second key is configured to extend through the second opening of the inner tube adjacent to the second notch of the acoustic waveguide.

14. The surgical instrument of claim 13, wherein the second notch is positioned angularly opposite from the first notch about the longitudinal axis on the surface of the acoustic waveguide.

15. The surgical instrument of claim 11, wherein the driver wrench is positioned between the rotational driver and the acoustic waveguide and thereby inhibits the rotational driver from direct contact with the acoustic waveguide.

16. A surgical instrument, comprising:
   (a) a body;
   (b) an end effector, including:
      (i) an ultrasonic blade, and
      (ii) a clamp arm; and
   (c) a shaft assembly extending between the body and the end effector defining a longitudinal axis and configured to rotatably couple with the body, wherein the clamp arm is movably coupled with the shaft assembly and distally extending therefrom, the shaft assembly, including:
- (i) an acoustic waveguide defining a first notch and a second notch,
- (ii) a rotational driver configured to rotate the shaft assembly relative to the body about the longitudinal axis, and
- (iii) a driver wrench operatively coupled between the rotational driver and the acoustic waveguide, wherein the driver wrench defines a first key and a second key, wherein the first and second keys are respectively received within the first and second notches thereby rotatably locking the driver wrench relative to the acoustic waveguide for rotating the shaft assembly relative to the body about the longitudinal axis.

17. A surgical instrument, comprising:
- (a) a body including a rotational drive channel;
- (b) an end effector, including:
  - (i) an ultrasonic blade, and
  - (ii) a clamp arm; and
- (c) a shaft assembly extending between the body and the end effector defining a longitudinal axis and configured to rotatably couple with the body, wherein the clamp arm is movably coupled with the shaft assembly and distally extending therefrom, the shaft assembly including:
  - (i) an elongated tube,
  - (ii) an acoustic waveguide positioned within the elongated tube and including a bore, and
  - (iii) a guide pin positioned within the bore and configured to be received within the rotational drive channel, wherein the guide pin is configured to rotatably lock the elongated tube to the acoustic waveguide and longitudinally lock the acoustic waveguide to the body for rotating the shaft assembly relative to the body about the longitudinal axis;

wherein the guide pin includes a base layer and a first insulating layer configured to insulate the base layer, wherein the base layer has a metal material forming a core, and wherein the first insulating layer has a silicone material.

18. The surgical instrument of claim 17, wherein the guide pin includes a second insulating layer configured to insulate the first insulating layer, and wherein the second insulating layer has a heat shrink material.

19. The surgical instrument of claim 17, wherein the body further includes a handle assembly having a clamp actuator operatively coupled to the clamp arm and configured to direct movement of the clamp arm relative to the ultrasonic blade.

20. The surgical instrument of claim 17, wherein the guide pin is configured to fully rotate around the longitudinal axis within the rotational drive channel.

\* \* \* \* \*